(12) United States Patent
Mirza et al.

(10) Patent No.: US 10,849,644 B2
(45) Date of Patent: *Dec. 1, 2020

(54) SURGICAL DEVICE

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 207 days.

This patent is subject to a terminal disclaimer.

(21) Appl. No.: 15/334,784

(22) Filed: Oct. 26, 2016

(65) Prior Publication Data
US 2017/0042566 A1    Feb. 16, 2017

Related U.S. Application Data

(63) Continuation-in-part of application No. 15/239,557, filed on Aug. 17, 2016, now Pat. No. 9,808,274,
(Continued)

(51) Int. Cl.
*A61B 17/32*    (2006.01)
*A61B 17/3211*    (2006.01)
(Continued)

(52) U.S. Cl.
CPC .. *A61B 17/320036* (2013.01); *A61B 1/00101* (2013.01); *A61B 1/00128* (2013.01);
(Continued)

(58) Field of Classification Search
CPC .... A61B 17/320016; A61B 17/320036; A61B 17/3205; A61B 1/00128; A61B 1/3132;
(Continued)

(56) References Cited

U.S. PATENT DOCUMENTS 3,537,451 A    11/1970    Beck et al.
3,885,560 A    5/1975    Baldwin
(Continued)

FOREIGN PATENT DOCUMENTS

EP    2725987 B1    10/2016
WO    2005032348 A2    4/2005
WO    2012/096746    7/2012

OTHER PUBLICATIONS

File history of U.S. Appl. No. 12/716,640, filed Mar. 3, 2010.
(Continued)

*Primary Examiner* — Erich G Herbermann
(74) *Attorney, Agent, or Firm* — Bodner & O'Rourke, LLP; Gerald T. Bodner; Christian P. Bodner

(57) ABSTRACT

An endoscopic surgical device for an endoscopic surgical procedure includes a slotted clear cannula with a tubular body having a distal end, a proximate end and a slot extending longitudinally therethrough. A pair of wings near the proximal end of the slotted clear cannula extend outward from the tubular body. The tubular body is made from a transparent material. The slotted clear cannula may be part of an endoscopic surgical blade assembly in which the cannula is attached to a housing enclosing a blade slidably oriented in the cannula. A kit comprising the endoscopic surgical device and a method for a performing a uniportal endoscopic surgical procedure using the endoscopic surgical device are also described.

2 Claims, 29 Drawing Sheets

Related U.S. Application Data which is a continuation of application No. 14/736,904, filed on Jun. 11, 2015, now Pat. No. 9,445,830, which is a continuation-in-part of application No. 14/477,478, filed on Sep. 4, 2014, which is a continuation of application No. 14/013,746, filed on Aug. 29, 2013, now Pat. No. 9,066,746, which is a continuation-in-part of application No. 13/790,016, filed on Mar. 8, 2013, now Pat. No. 8,911,470, which is a continuation-in-part of application No. 13/602,968, filed on Sep. 4, 2012, which is a continuation of application No. 12/716,640, filed on Mar. 3, 2010, now Pat. No. 8,827,893, which is a continuation-in-part of application No. 12/400,485, filed on Mar. 9, 2009, now Pat. No. 8,821,383.

(51) Int. Cl.
| | | |
|---|---|---|
| *A61B 1/313* | (2006.01) | |
| *A61B 1/00* | (2006.01) | |
| *A61B 1/018* | (2006.01) | |
| *A61B 17/3205* | (2006.01) | |
| *A61B 17/00* | (2006.01) | |

(52) U.S. Cl.
CPC .......... *A61B 1/00154* (2013.01); *A61B 1/018* (2013.01); *A61B 1/3132* (2013.01); *A61B 17/32002* (2013.01); *A61B 17/3205* (2013.01); *A61B 17/3211* (2013.01); *A61B 17/320016* (2013.01); *A61B 2017/00353* (2013.01); *A61B 2017/320008* (2013.01); *A61B 2017/320052* (2013.01); *A61B 2017/320064* (2013.01); *A61B 2017/32113* (2013.01)

(58) Field of Classification Search
CPC .... A61B 2017/320064; A61B 1/00101; A61B 1/00154; A61B 1/018; A61B 17/32002; A61B 17/3211; A61B 2017/00353; A61B 2017/320008; A61B 2017/320052; A61B 2017/32113
USPC ......... 606/170–172, 1, 79–85, 167; 600/564, 600/106, 104, 570; 7/158; 81/439, 440; 30/162, 163, 153
See application file for complete search history.

(56) References Cited

U.S. PATENT DOCUMENTS

| | | | |
|---|---|---|---|
| 4,324,236 A | 4/1982 | Gordon et al. | |
| 4,683,879 A | 8/1987 | Williams | |
| 4,962,770 A | 10/1990 | Agee et al. | |
| 4,963,147 A | 10/1990 | Agee et al. | |
| 5,141,497 A | 8/1992 | Erskine | |
| 5,179,963 A | 1/1993 | Berger et al. | |
| 5,197,971 A * | 3/1993 | Bonutti | A61B 17/0218 604/105 |
| 5,273,024 A | 12/1993 | Menon et al. | |
| 5,282,816 A | 2/1994 | Miller et al. | |
| 5,295,974 A | 3/1994 | O'Laughlin | |
| 5,322,055 A | 6/1994 | Davison et al. | |
| 5,323,765 A | 6/1994 | Brown | |
| 5,325,883 A * | 7/1994 | Orr | A61B 17/320036 128/898 |
| 5,366,465 A | 11/1994 | Mirza | |
| 5,447,513 A | 9/1995 | Davison et al. | |
| 5,489,273 A | 2/1996 | Whitney et al. | |
| 5,569,283 A | 10/1996 | Green et al. | |
| 5,578,051 A | 11/1996 | Mirza | |
| 5,595,410 A | 1/1997 | Wilson et al. | |
| 5,620,446 A | 4/1997 | McNamara et al. | |
| 5,649,946 A | 7/1997 | Bramlet | |
| 5,651,790 A | 7/1997 | Resnick et al. | |
| 5,665,093 A | 9/1997 | Atkins et al. | |
| 5,720,763 A | 2/1998 | Tovey | |
| 5,730,749 A | 3/1998 | Battenfield | |
| 5,743,882 A | 4/1998 | Luther | |
| 5,755,713 A * | 5/1998 | Bilof | A61B 17/00234 600/104 |
| 5,827,312 A | 10/1998 | Brown et al. | |
| 5,840,013 A | 11/1998 | Lee et al. | |
| 5,848,013 A | 12/1998 | Caser et al. | |
| 5,879,334 A | 3/1999 | Brimhall | |
| 5,908,431 A | 6/1999 | Battenfield | |
| 5,908,433 A | 6/1999 | Eager et al. | |
| 5,910,105 A | 6/1999 | Nahen et al. | |
| 5,968,061 A * | 10/1999 | Mirza | A61B 17/320036 604/171 |
| 6,139,532 A | 10/2000 | Howell et al. | |
| 6,283,948 B1 | 9/2001 | McKernan et al. | |
| 6,402,677 B1 | 6/2002 | Jacobs | |
| 6,589,231 B1 | 7/2003 | Gobron et al. | |
| 6,613,065 B2 | 9/2003 | Swain et al. | |
| 6,685,717 B1 | 2/2004 | Ilic | |
| 6,869,112 B2 * | 3/2005 | Guidetti | F16B 2/246 280/823 |
| 7,041,115 B2 | 5/2006 | Mirza et al. | |
| 7,780,690 B2 | 8/2010 | Rehnke | |
| 8,252,011 B1 | 8/2012 | Forrester et al. | |
| 8,672,960 B2 | 3/2014 | Briganti et al. | |
| 2002/0019611 A1 | 2/2002 | Green | |
| 2002/0123724 A1 | 9/2002 | Douglas et al. | |
| 2004/0098005 A1 * | 5/2004 | Mirza | A61B 17/320016 606/170 |
| 2004/0230155 A1 | 11/2004 | Blanco et al. | |
| 2005/0137528 A1 | 6/2005 | Wilkinson | |
| 2007/0288043 A1 * | 12/2007 | Rehnke | A61B 1/313 606/170 |
| 2008/0045905 A1 | 2/2008 | Chawki | |
| 2008/0045989 A1 | 2/2008 | Welborn | |
| 2008/0065124 A1 | 3/2008 | Olson | |
| 2009/0043270 A1 | 2/2009 | Noyce et al. | |
| 2009/0306541 A1 | 12/2009 | Kano et al. | |
| 2010/0228083 A1 | 9/2010 | Mirza et al. | |
| 2010/0228085 A1 | 9/2010 | Mirza et al. | |
| 2011/0046652 A1 | 2/2011 | Rehnke et al. | |
| 2011/0130779 A1 * | 6/2011 | Mirza | A61B 1/018 606/170 |
| 2014/0066709 A1 | 3/2014 | Mirza et al. | |
| 2014/0371526 A1 | 12/2014 | Mirza et al. | |
| 2015/0282832 A1 | 10/2015 | Mirza et al. | |
| 2016/0354103 A1 | 12/2016 | Mirza et al. | |

OTHER PUBLICATIONS

File history of U.S. Appl. No. 13/790,016, filed on Mar. 8, 2013.
File history of U.S. Appl. No. 13/602,968, filed on Sep. 4, 2012.
File history of U.S. Appl. No. 12/400,485, filed Mar. 9, 2009.
File history of U.S. Appl. No. 15/239,557, filed Aug. 17, 2016.
File history of U.S. Appl. No. 14/736,904, filed Jul. 11, 2015.
File history of U.S. Appl. No. 14/013,746, filed Aug. 29, 2013.
File history of U.S. Appl. No. 14/477,478, filed Aug. 26, 2016.
International Search Report and Written Opinion of the International Searching Authority issued in International Patent No. PCT/US2016/058917 dated Apr. 4, 2017.

* cited by examiner

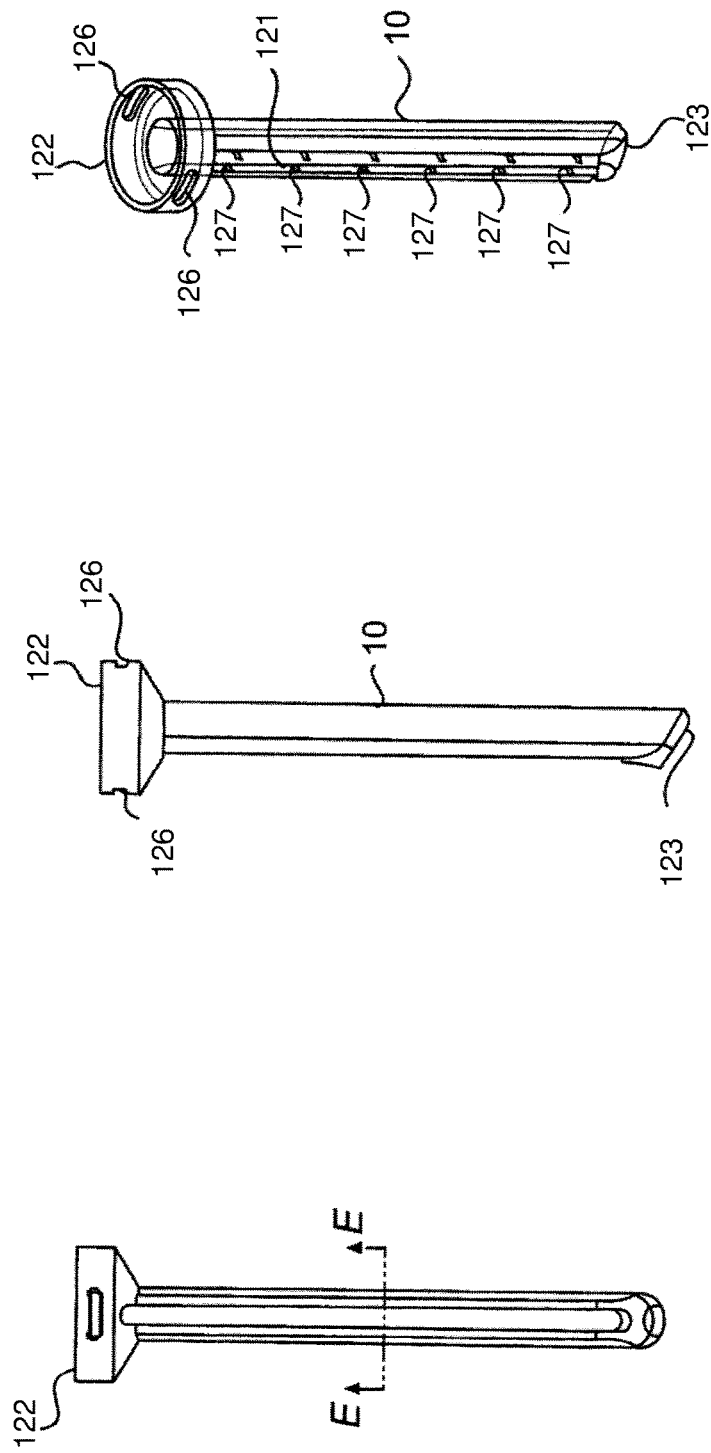

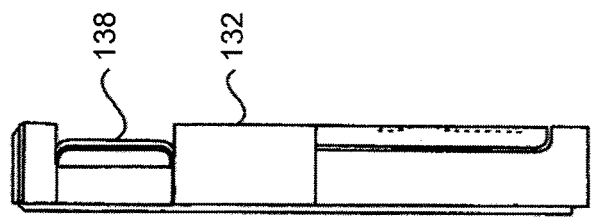
FIG. 28D
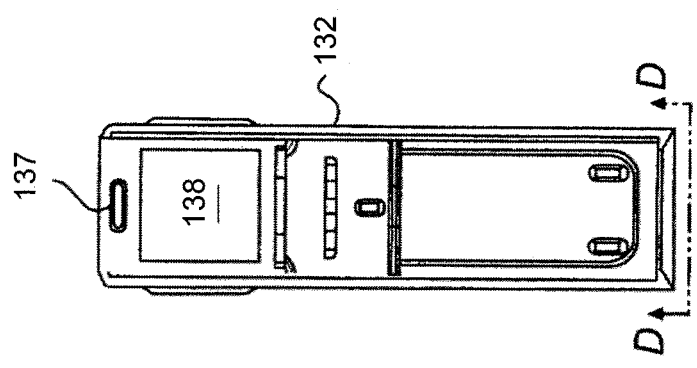
FIG. 28C
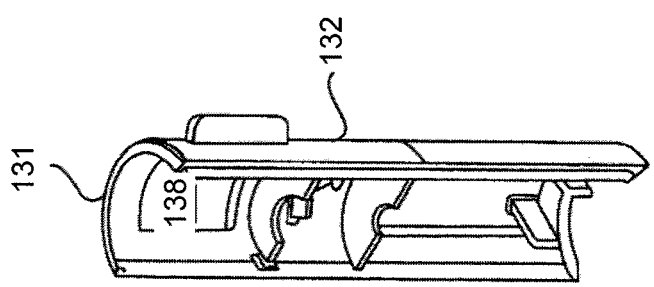
FIG. 28B
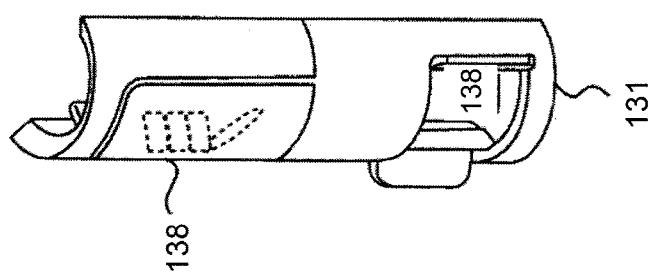
FIG. 28A
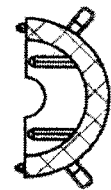
FIG. 28F
FIG. 28E

SURGICAL DEVICE

This application is a continuation-in-part of application Ser. No. 15/239,557, filed on Aug. 17, 2016, which is a continuation of application Ser. No. 14/736,904, filed on Jun. 11, 2015, now U.S. Pat. No. 9,445,830, which is a continuation of application Ser. No. 14/013,746, filed on Aug. 29, 2013, now U.S. Pat. No. 9,066,746, which is a continuation-in-part of application Ser. No. 13/790,016, filed Mar. 8, 2013, now U.S. Pat. No. 8,911,470, which is a continuation-in-part of application Ser. No. 13/602,968, filed on Sep. 4, 2012. This application is also a continuation-in-part of application Ser. No. 14/477,478, filed on Sep. 4, 2014, which is a continuation of U.S. patent application Ser. No. 12/716,640, filed on Mar. 3, 2010, now U.S. Pat. No. 8,827,893, which is a continuation-in-part application of U.S. patent application Ser. No. 12/400,485, filed on Mar. 9, 2009, now U.S. Pat. No. 8,821,383. The entirety of the aforementioned applications is incorporated herein by reference.

FIELD

This application generally relates to medical devices. In particular, the application relates to devices and methods for endoscopic surgery, e.g., for endoscopic tunnel or pulley release surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Trigger finger is characterized by catching, snapping or locking of the involved finger flexor tendon, associated with dysfunction and pain. Localized inflammation or nodular swelling of the flexor tendon causes a disparity in size between the flexor tendon and the surrounding retinacular pulley system, most commonly at the level of the first annular (A1) pulley. When the subject extends the involved finger, the tendon will "catch" on the pulley, followed by an abrupt popping of the tendon through the pulley. This results in a difficulty flexing or extending the finger and the "triggering" phenomenon. Typically, a first course of treatment for trigger finger is corticosteroid injections into the tendon sheath to reduce inflammation. When corticosteroid injection is not or no longer effective, surgical division of the A1 pulley is indicated.

Carpal tunnel syndrome is an entrapment median neuropathy resulting from compression of the median nerve at the wrist in the carpal tunnel. Symptoms of carpal tunnel syndrome include tingling, numbness, weakness, or pain felt in the fingers supplied by the median nerve or in the palm. Repetitive tasks, force, posture, and vibration have been cited as causative or contributing factors to carpal tunnel syndrome. Palliative treatments for carpal tunnel syndrome include direct corticosteroid injections, splinting, oral corticosteroids and/or behavior modification. Failure of these methods within a reasonable period of time, and/or the presence of other contributing factors, indicates a need for surgical division of the carpal tunnel.

Other conditions involving the compression of a nerve by a ligament pulley or tunnel include Guyon's canal (or canal) syndrome, which is a compression of the ulnar nerve as it passes through Guyon's canal at the wrist; cubital tunnel syndrome, which is a compression of the ulnar nerve as it passes through the cubital tunnel at the elbow; radial tunnel syndrome, which is a compression of the radial nerve as it travels from the brachial plexus to the wrist and hand; and pronater teres syndrome, which is a compression neuropathy of the median nerve in the region of the elbow.

Conventional surgical techniques and equipment for pulley or tunnel release require a fairly large incision over the pulley or tunnel and spreading of the incision to allow viewing and instrument access. These techniques can require a longer period of recovery than endoscopic methods and have greater levels of post-operative pain due to the incision size and level of manipulation during the procedure.

Typically, endoscopic surgery has involved a number of steps and separate devices for performing pulley or tunnel division. After making an incision and opening a path to the pulley or tunnel using a blunt instrument, a cannula is inserted into the path. Briefly, in order to smoothly insert the cannula, the central lumen of the cannula must be filled with a device, such as an obturator. The obturator is then removed and an endoscope, or arthroscope, is inserted into the cannula to view the pulley or tunnel. The endoscope is then withdrawn from the cannula, a knife is either advanced into the cannula for division or a specialized knife assembly is affixed to the endoscope and the knife/endoscope assembly is advanced into the cannula for division. The present application fulfills a need in the art for a compact device for uniportal endoscopic pulley or tunnel release surgery that eliminates the need for a separate device, such as an obturator, for filling the cannula during insertion and eliminates the need to remove the endoscope in order to insert a blade or blade assembly.

SUMMARY

One aspect of the present invention relates to a device specifically designed for an endoscopic surgical procedure selected from the group consisting of carpal tunnel release, cubital tunnel release, plantar fascia release, lateral release for patella realignment, release of radial tunnel, release of pronatar teres, release of trigger finger, release of lacertous fibrosis, release of the extensor tendons for lateral epicondylitis, release of medial epicondylitis, release of the posterior and other compartments of the leg, forearm fascia release for fascial compartment syndrome, and release of fascial compartments in the upper and lower extremity.

In one embodiment, the device includes a slotted clear cannula having a tubular body with distal and proximate ends, an open slot extending longitudinally therethrough. The cannula further include a pair of wings formed on or near the proximate end of the tubular body or they may be connected to the tubular body, extending outward from the tubular body. The wings may be. In some embodiments, the tubular body is made from a transparent material and has an inner diameter large enough to accommodate an endoscope. In some embodiments, the tubular body has an inner diameter from about 1-10 mm, an outer diameter from about 2-12 mm, a length from about 5-25 cm, or combination thereof. In some embodiments, the tubular body is made from a transparent plastic material selected from the group consisting of polyacrylate, polycarbonate, polystyrene, glycol modified polyethylene terephthalate, and cellulose acetate butyrate.

In another aspect, the device relates to an endoscopic surgical blade assembly with a slotted clear cannula according to the present application. In one embodiment, the endoscopic surgical blade assembly includes: (a) a housing having a proximate end and a distal end; (b) a slotted clear cannula attached to the distal end of the housing, the slotted clear cannula comprises a cannula body having a proximate end and a distal end, and a slot extending from the proximate end of the cannula to the proximity of the distal end of the cannula; (c) a revolver assembly located within the housing, comprising: a slide lock having a proximate end, a distal end and two notches at the distal end; a scraper; a blade assembly; and a circular revolver body comprising a selector switch; wherein the scraper and the blade reside at the two notches of the slide lock in a pre-deployment position and wherein the selector switch allows selection of the scraper or the blade for deployment; (d) a tube assembly having a proximate end and a distal end, the distal end of the tube assembly is located within the housing and extends through the revolver, the distal end of the tube assembly is capable of entering the slotted clear cannula from the proximate end of the clear cannula; and (e) a scope lock assembly for holding a viewing device in a stationary position relative to the tube assembly.

In another aspect, the present application relates to an instrument kit for implementing an endoscopic surgical procedure with a transparent cannula. The instrument kit includes a transparent cannula guide member including a longitudinal bore having open proximal and distal ends and an open slot extending along the length thereof communicating with the open ends; and an elongate insertion member being slidably receivable within the cannula guide member and being configured so that at least portions thereof conform with the open distal end and the open slot of the guide member to form a smooth exterior surface in combination therewith, wherein the elongate insertion member is an endoscope sized for insertion into the cannula guide member for direct visualization of an operative site.

In some embodiments, the instrument kit further includes a knife configured for slidable movement through the cannula guide member.

In one embodiment, the distal end of the endoscope is configured for mounting a cutting instrument, depth gauge, or both thereon. The instrument kit further comprises a rasp member sized for insertion into the cannula guide member, a curved dissector, or both.

In certain embodiments, the instrument kit further includes a locking device capable of locking the endoscope and the cannula guide member into mutually fixed positions, a stop device mountable on the cannula guide member to prevent excessive penetration at a surgical site by a cutting instrument, or both.

In another aspect, a method for implementing a uniportal endoscopic surgical procedure with a surgical device according to the present application includes the steps of: establishing an entry portal in the subject at a location proximate to an operation site; inserting into the entry portal an elongated cannula having a tubular body with an open proximal end, an integrally formed open slot extending longitudinally from proximal end to the proximity of the distal end; extending the elongated cannula through the entry portal to the target tissue; advancing an endoscope into the cannula to visualize a target tissue; and advancing a blade into the cannula until a desired cut is made on the target tissue. In some embodiments, the method further includes the steps of making an incision to establish an entry portal at a location proximal to a ligament in need of repair; forming a pathway beneath the ligament; inserting the elongated cannula into the pathway; visualizing the ligament with an endoscope; dividing the ligament with a cutting instrument protruding through the open slot of the elongated cannula by single-handed manipulation of the endoscope and cutting instrument; and withdrawing the elongated cannula through the entry portal. In some embodiments, the entry portal is established proximal to the target tissue. In some embodiments, the entry portal is established distal to the target tissue.

BRIEF DESCRIPTION OF THE DRAWINGS

The present application can be better understood by reference to the following drawings. The drawings are merely exemplary to illustrate certain features that may be used singularly or in combination with other features and the present application should not be limited to the embodiments shown.

Figure 19:
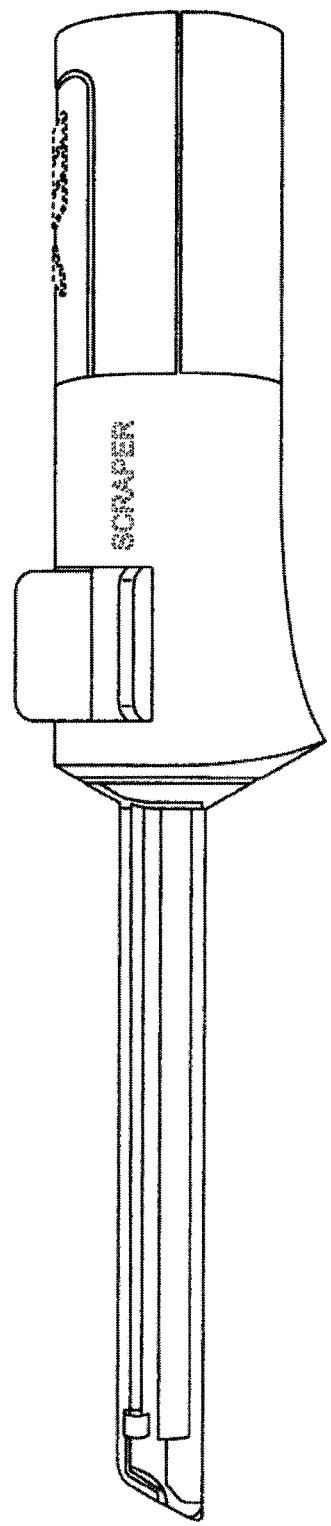
FIG. 19 is a perspective view of another embodiment of the device of the present application.

E) and end view (B, D, F) of the embodiment of FIG. 19 for the advancement of an endoscope alone (A, B), an endoscope with a scraper (C, D) or an endoscope with a blade (E, F).

Figure 25:
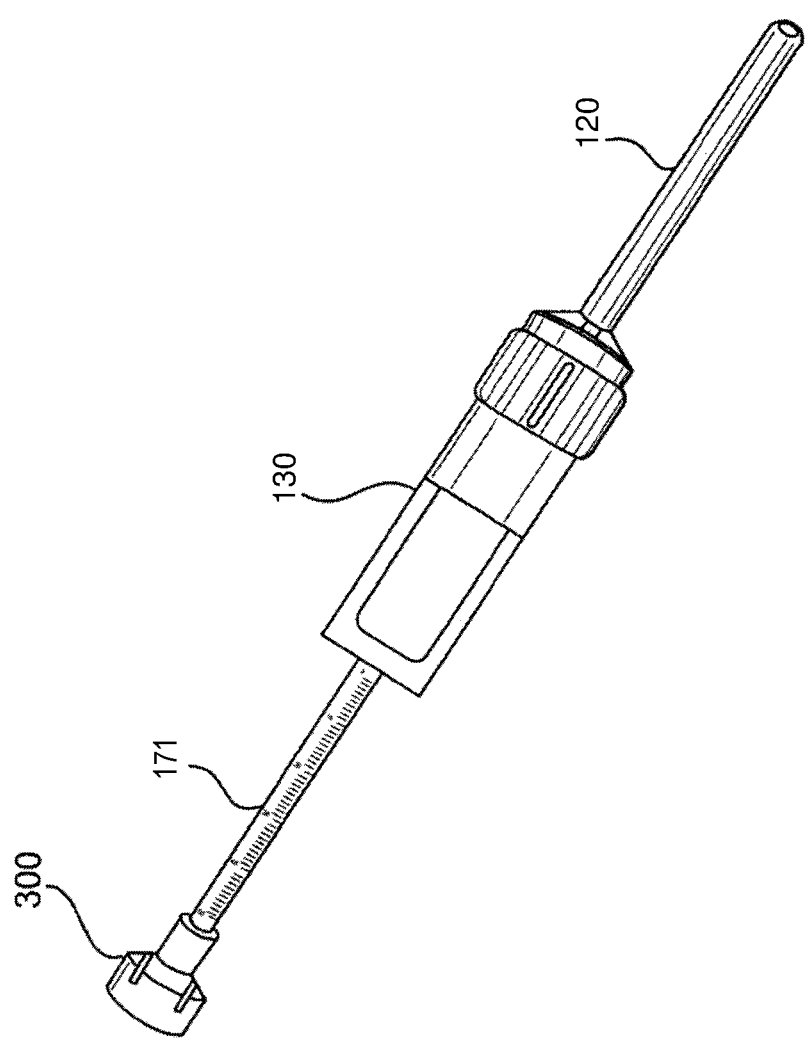

FIG. 25 is a perspective view of another embodiment of the device of the present application.

Figure 26:
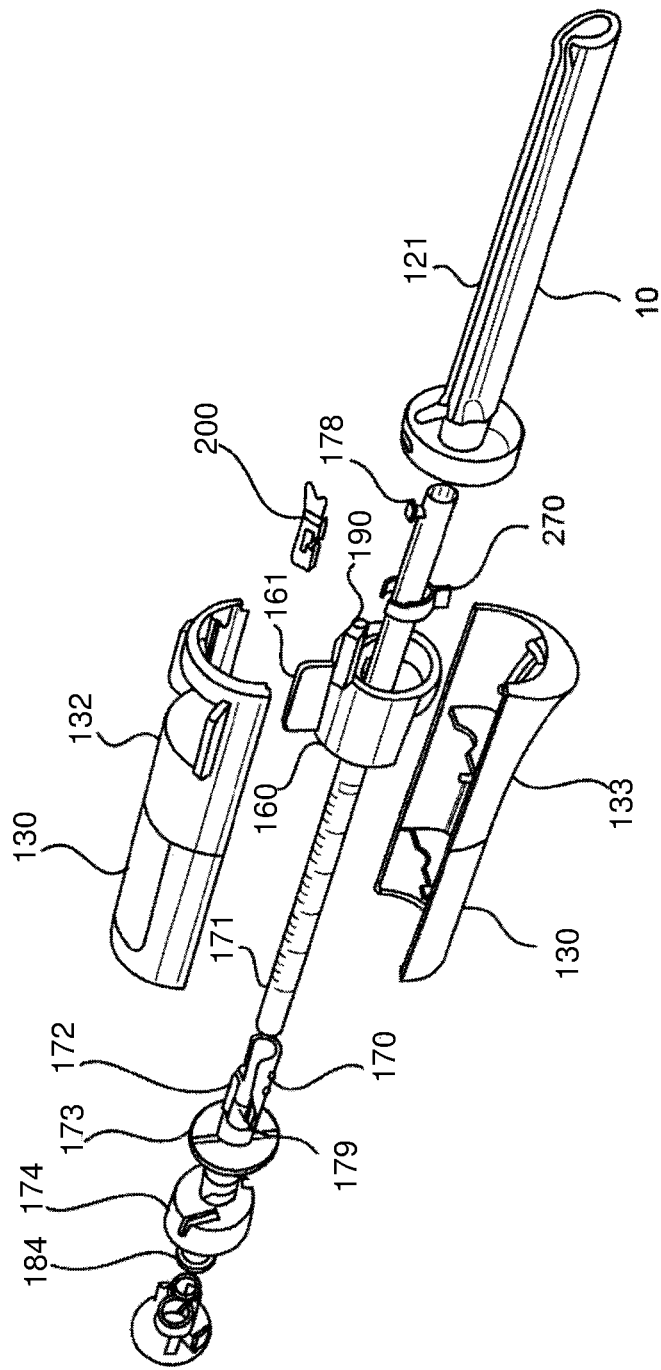

FIG. 26 is an exploded view of the embodiment depicted in FIG. 25.

FIGS. 27A-E show perspective and cross-sectional views of the cannula element of the embodiment depicted in FIG. 25.

FIGS. 28A-F show perspective and cross-sectional views of the top shell of the housing of the embodiment depicted in FIG. 25.

FIGS. 29A-F show perspective and cross-sectional views of the bottom shell of the housing of the embodiment depicted in FIG. 25.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention.

Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

The term "trigger finger," as used herein, also refers to "trigger digit," "trigger thumb," and "stenosing tendovaginitis."

As used herein, the terms "horizontal" and "vertical," and derivatives of those terms, are used in respect to their relationship to the plane defined by the slot in the cannula of the present application. "Vertical" refers to the plane that can, for example, pass through the slot of the cannula and bisect the cannula into two equal halves, while "horizontal" refers to a plane that is perpendicular to the vertical plane. The horizontal plane may be a level plane with respect to the length of the cannula or housing of the device, or may be at an angle to that level plane, allowing some upward or downward movement of elements moving along the horizontal plane with respect to the level plane.

One aspect of the present application relates to a slotted transparent cannula or guide member specifically designed for endoscopic surgical procedures. Non-limiting examples of endoscopic surgical procedures include carpal tunnel release, cubital tunnel release, plantar fascia release, lateral release for patella realignment, release of radial tunnel, release of pronatar *teres*, release of trigger finger, release of lacertous fibrosis, release of the extensor tendons for lateral epicondylitis, release of medial epicondylitis, release of the posterior and other compartments of the leg, forearm fascia release for fascial compartment syndrome, and release of fascial compartments in the upper and lower extremity.

The slotted transparent cannula comprises a tubular body with a proximal end and a distal end, a passage way within the tubular body, a slot extending longitudinally from the proximal end or the proximity of the proximal end to the distal end or the proximity of the distal end, and one or more wings or extrusions. The one or more wings or extrusions are formed on, or connected to, the proximal end or the proximity of the proximal end and extending outward from the tubular body. In some embodiments, the one or more wings may be substantially coplanar or non-coplanar with the tubular body. In some embodiments, the one or more wings are replaced with one or more outwardly extending curvilinear flange portions. The one or more wings or curvilinear flange portions may be made of a transparent or non-transparent material.

In some embodiments, the slotted transparent cannula comprises a transparent tubular body with a single wing formed integrally on, or connected to, the proximal end or the proximity of the proximal end of the tubular body. The wing may be made of a transparent or non-transparent material. In some embodiments, the wing is substantially coplanar with the tubular body. In some embodiments, the wing is substantially non-coplanar with the tubular body. In some embodiments, the wing is replaced with an outwardly extending curvilinear flange.

Figure 1:
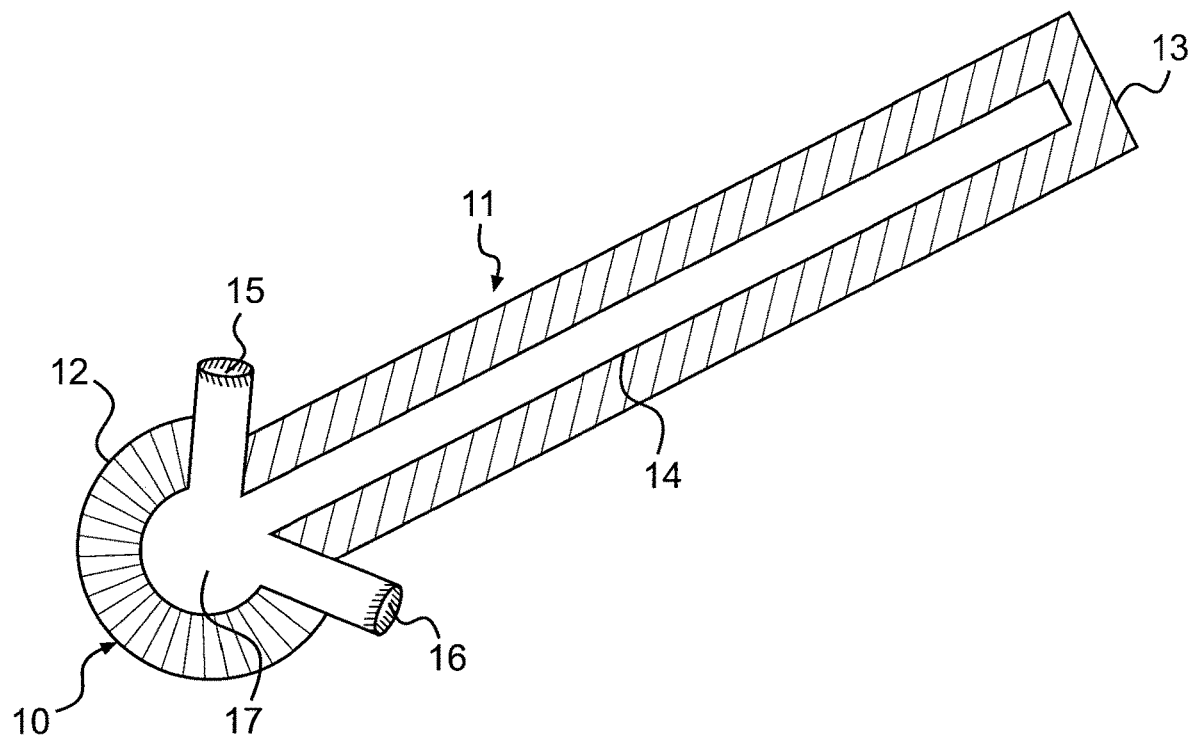
FIG. 1 illustrates a three-dimensional view of an embodiment of a slotted transparent cannula.

In one embodiment depicted in FIG. 1, the cannula 10 has a transparent tubular body 11 with a proximal end 12 and a distal end 13; a slot 14 extending longitudinally therethrough; and a pair of wings formed on or near the proximate end of the slotted clear cannula, the wings extending outward from the tubular body. In some embodiments, the wings extends radially from the tubular body. In some embodiments, the wings are formed as a flattened extension towards both sides of the tubular body. The slot 14 may start at or near the beginning of the proximate end of the tubular body 11 so that an instrument with a matching structure, such as a protrusion, can be inserted into the cannula 10 from the proximate end of the tubular body. The slot 14 may end a short distance from the distal end of the tubular body 11 to prevent excessive advancement of cannula mounted surgical tools, such as obturators or blades at the surgical site.

Figure 2:
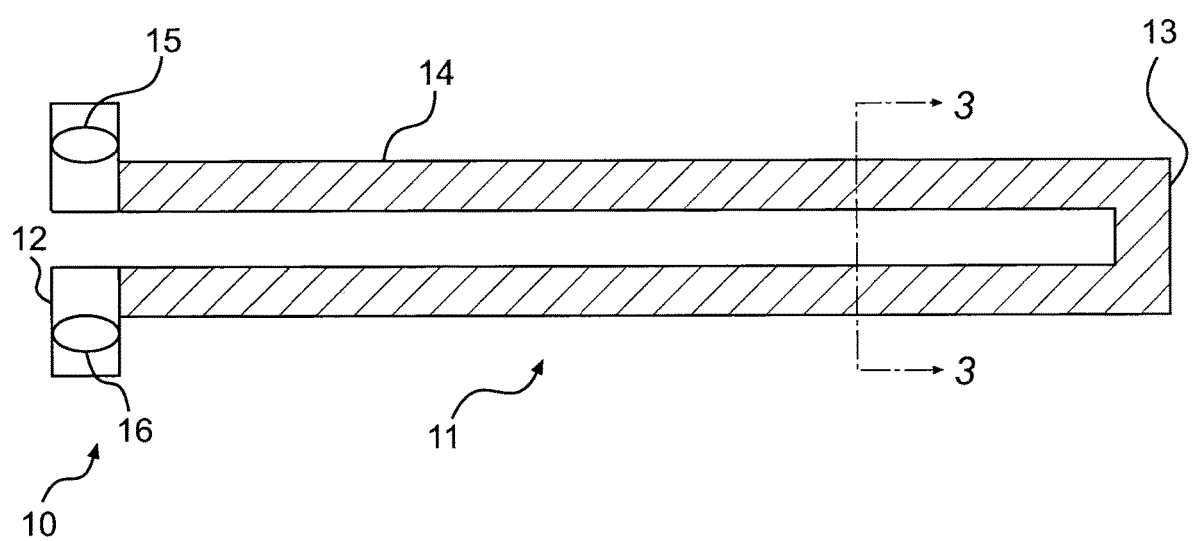
FIG. 2 illustrates a top view of the slotted transparent cannula.
Figure 3:
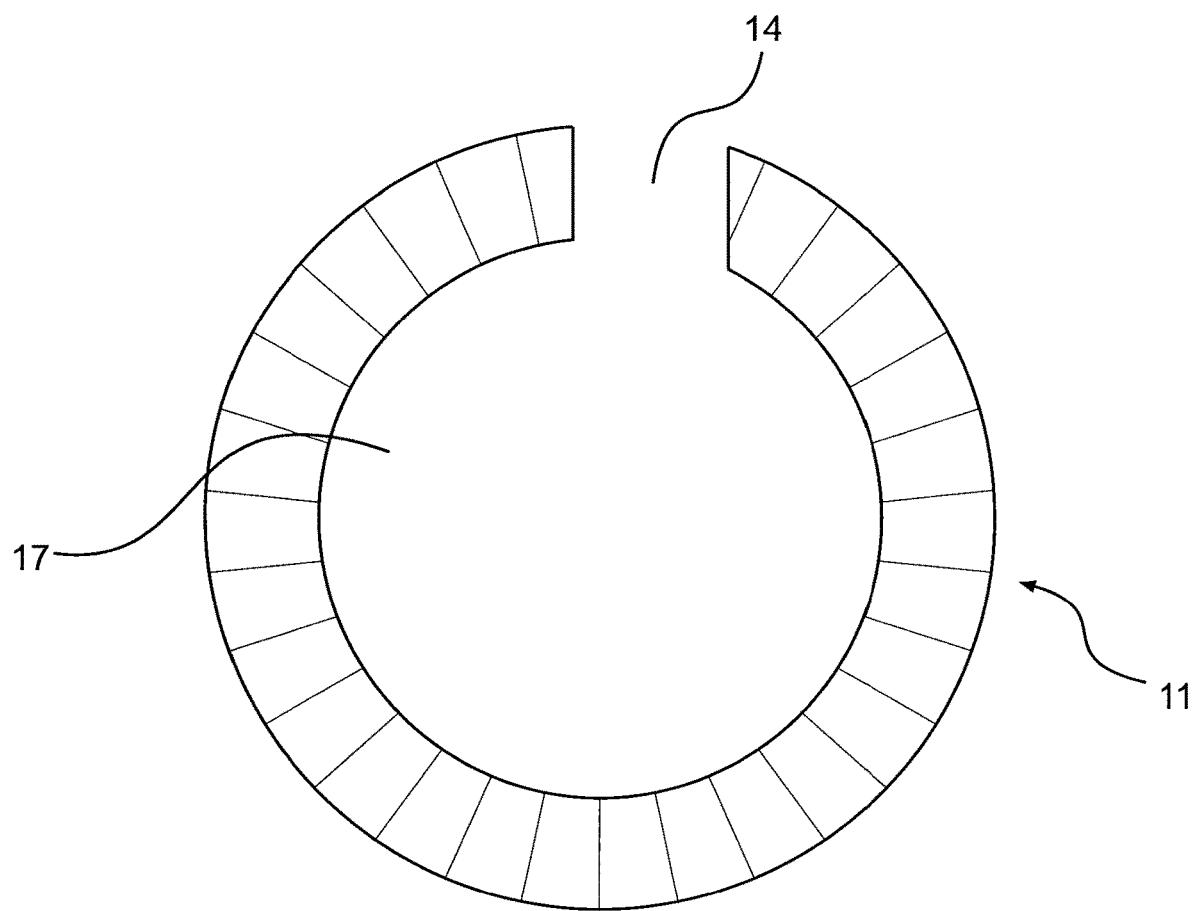
FIG. 3 illustrates a sectional view taken along line 3-3 in FIG. 2.

FIGS. 2 and 3 show an embodiment of the clear cannula of the present application. In this embodiment, the tubular body 11 of the cannula 10 is circular in cross-sectional configuration and has one or more apertures 17 to facilitate passage of an endoscope or other surgical devices. In one embodiment, the cannula 10 has a single central aperture 17 sized to allow passage of a surgical instrument, such as an obturator or endoscope with sufficient clearance. In one embodiment, the central aperture has a diameter of 1-10 mm, preferably 2-8 mm, and more preferably 2-5 mm. The aperture 17 near the proximal end 12 of the tubular body 11 may be open or closed.

While FIG. 2 shows a substantially circular central aperture 17, the central aperture can have a cross-section of any shape or depth, so long as it allows the passage of an endoscope of other surgical devices. In certain embodiments, the distal end of the slot may be tapered downward at an angle to better retain the blade or knife in the slot and prevent it from rising up out of the slot to inadvertently engage tissues. In one embodiment, the tubular body has an inner diameter in the range of 1-10 mm, preferably 2-8 mm, and more preferably 2-5 mm. In another embodiment, the tubular body has an outer diameter in the range of 2-12 mm, preferably 4-10 mm, and more preferably 4-7 mm. In another embodiment, the tubular body has a length in the range of 5-25 cm, preferably 12-18 cm, and more preferably 10-15 cm. The slot 14 allows a controlled movement of a passage of a surgical blade through the central aperture 17. The slot 14 may have a width in the range of 1-10 mm, 1-6 mm, 1.5-5 mm, or 2-4 mm. In certain embodiments, the tubular body further comprises one or more observation holes.

The wings 15 and 16 in FIGS. 1-2 are depicted as being integral to the tubular body 11 that extend outward radially from the tubular body 11 to provide holding points for the cannula 10. Alternatively, the wings 15, 16 may be connectively joined to the tubular body 11. The angle between the outwardly extending wings 15 and 16 may range between 90 degrees to 180 degrees. Thus, the wings 15, 16 may be substantially coplanar or non-coplanar with the tubular body In some embodiments, the wings 15 and 16 are flat wings extending outwardly from the tubular body. In other embodiments, the wings 15 and 16 may be replaced with one or more outwardly extending curvilinear flange portions. In one embodiment, the flange portions are curved to match the curvature of the proximate end of an obturator. In another embodiment, the wings 15 and 16 are replaced with a single outwardly extending curvilinear flange. In another embodiment, the clear cannula 10 contains a single wing extending outwardly from the cannula body 11. In another embodiment, the distal end of the cannula 10 is configured to form an integral obturator and dissector, thereby eliminating separate components.

In some embodiments, the tubular body 11 includes two longitudinal slots 14 disposed along a horizontal axis and separated by a partition, such that a first slot is configured for accepting a scope, such as an endoscope or arthroscope, and a second slot is configured for accepting a cutting instrument. The partition helps prevent the endoscope and knife from inadvertently interfering with each other. One or both of the longitudinal slots 14 may be open for most of the longitudinal length. In certain embodiments, a proximal portion of one or both of the longitudinal slots may be covered, forming an enclosed tunnel region connecting the open slot along the distal side with a luminal portion extending therefrom, terminating in an opening (open aperture) at the proximal end of the tubular body through which instruments can be passed. In other embodiments, there is not an opening at the proximal end 12 of the tubular body 11. Instead, the proximal end of the slot 14 begins downstream of the proximal end 12 of the tubular body 11.

In one embodiment, the tubular body 11 include two longitudinal slots disposed along a vertical axis (one on top of the other) for two instruments (e.g., two endoscopes), next to a third longitudinal slot for accepting the cutting instrument. In this embodiment, the first two slots may be configured to provide multiple views from the endoscope relative to the cutting instrument, or simply another aperture for passing an additional surgical instrument. A proximal portion of one or both of these first two longitudinal slots may be covered so as to form an enclosed tunnel region connecting an open slot portion toward the distal side with a luminal portion defining one or two openings (open apertures) at the proximal end of the tubular body through which instruments can be passed, as opposed to closed slot 14 ends beginning downstream of the proximal end 12 of the tubular body 11.

The tubular body 11 of the cannula 10 is made from a transparent material and has an inner diameter large enough for passage of an endoscope, knife, cutting blade, rasp, probe, and/or other endoscopic tool to pass therethrough. As used hereinafter, the term "transparent plastic material" refers to a polymer material that has a light transmission rate equal to, or greater than, 80%. Preferably, the transparent plastic material has a light transmission rate equal to, or greater than, 90%.

The transparency of the cannula wall makes it possible to observe the anatomical structure around the insertion path with an endoscope. The plastic cannula is lightweight and can be made by injection molding to reduce cost. The transparent plastics used in the present application should have good impact resistance and abrasion resistance. In one embodiment, the transparent plastics may be coated with a cover layer such as alumina or diamond like carbon, to improve abrasion resistance. The tubular body may further contain observation holes for better identification of the surrounding tissue. In one embodiment, the observation holes are oblong openings on the opposite side of slot 14.

Examples of transparent plastics include, but are not limited to, a polyacrylate such as polymethlamethacrylate, a polycarbonate, a polystyrene, a glycol modified polyethylene terephthalate, and a cellulose acetate butyrate. Transparent plastics are commercially available under the tradenames of ACRYSTEX®, NAS®, EMPERA®, KIBITON®, ZYLAR®, ZYTEL®, etc.). The transparent cannula 10 can be used in combination with a variety of surgical instruments. Although these instruments have been shown in the Mirza U.S. Pat. Nos. 5,366,465, 5,578,051, 5,968,061 and 7,041,115, some of these instruments are described in detail herein for purposes of clarity.

Figure 4:
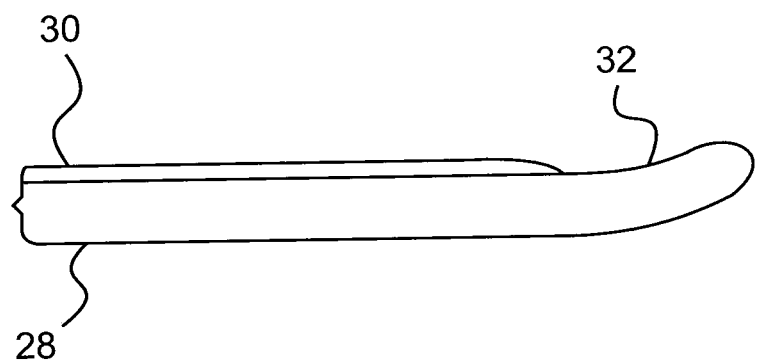
FIG. 4 illustrates a longitudinal side view of the leading end of an obturator adapted to be inserted into the slotted cannula of FIG. 1.
Figure 5:
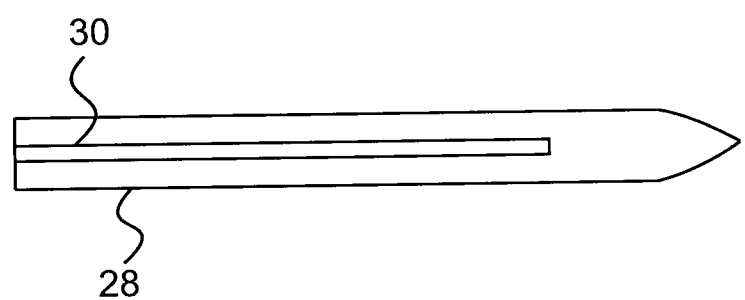
FIG. 5 illustrates a top view of the leading end of the obturator.

FIGS. 4 and 5 show an obturator 28 that is adapted to be slidably received within the cannula body 11, and presents a smooth outer surface through the intermediary of an axial, upstanding rib portion 30 which is engageable in close conformance within the longitudinal slot 14 of the cannula upon insertion therein. The distal end of the obturator 28 is a tapered tip portion 32 which is bent upwardly in a direction towards the longitudinal rib to impart to the tip a somewhat upward curvature.

Figure 6:
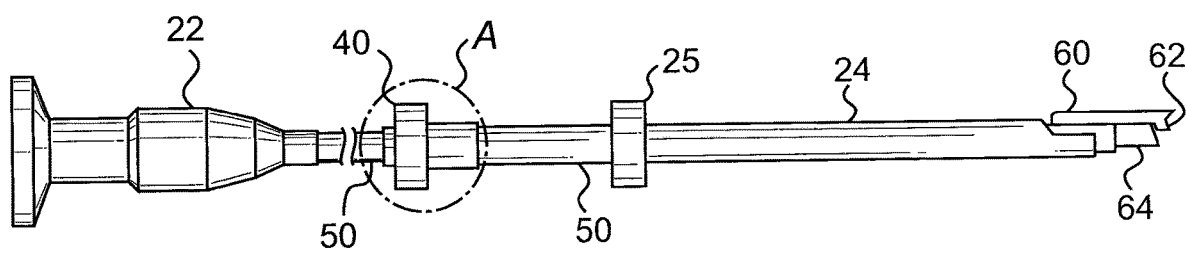
FIG. 6 illustrates a longitudinal side view of the endoscopic instrument, showing the scope and cutting device mounted on the latter inserted into the slotted cannula.
Figure 7:
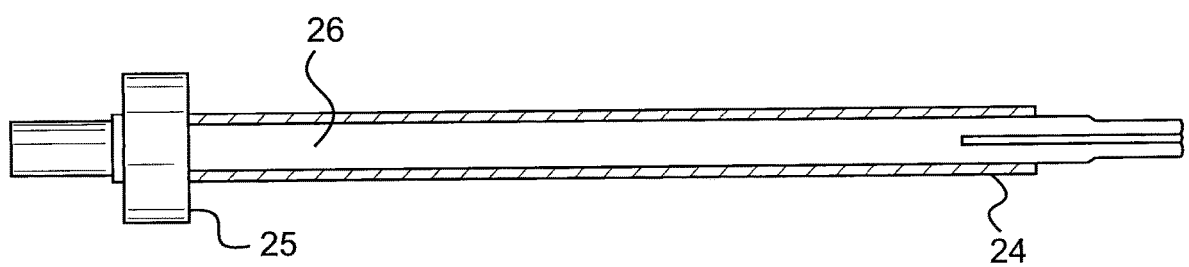
FIG. 7 illustrates a top view of the leading section of the endoscopic instrument shown in FIG. 6.
Figure 8:
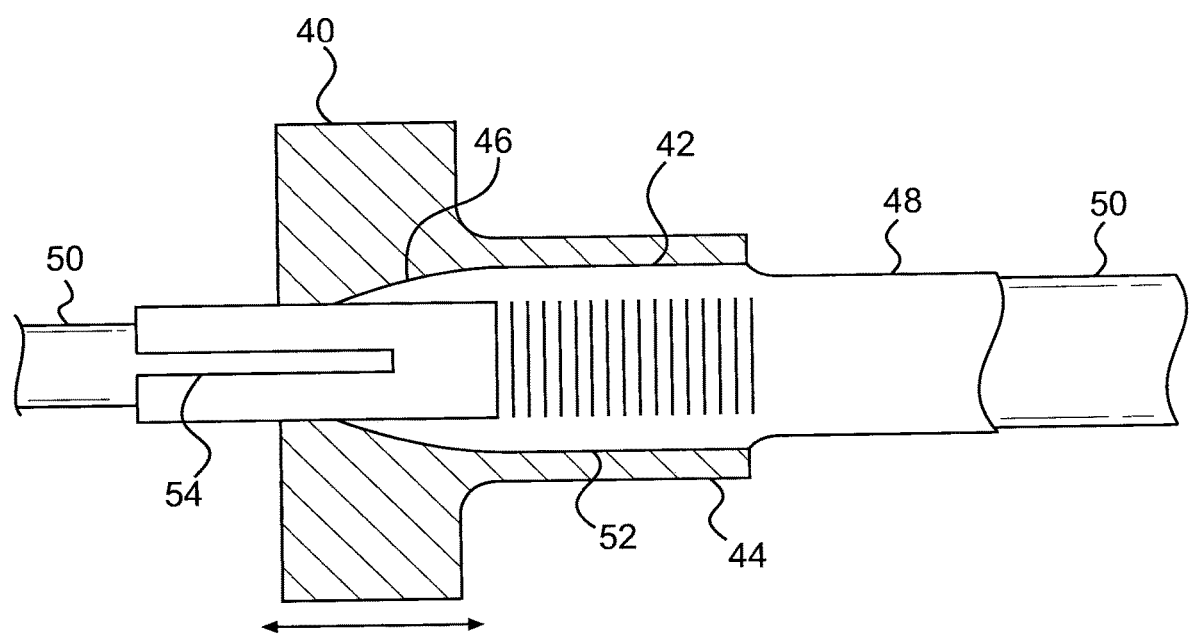
FIG. 8 illustrates, on a somewhat enlarged scale, a sectional view of the encircled portion A of the instrument of FIG. 6.
Figure 9:
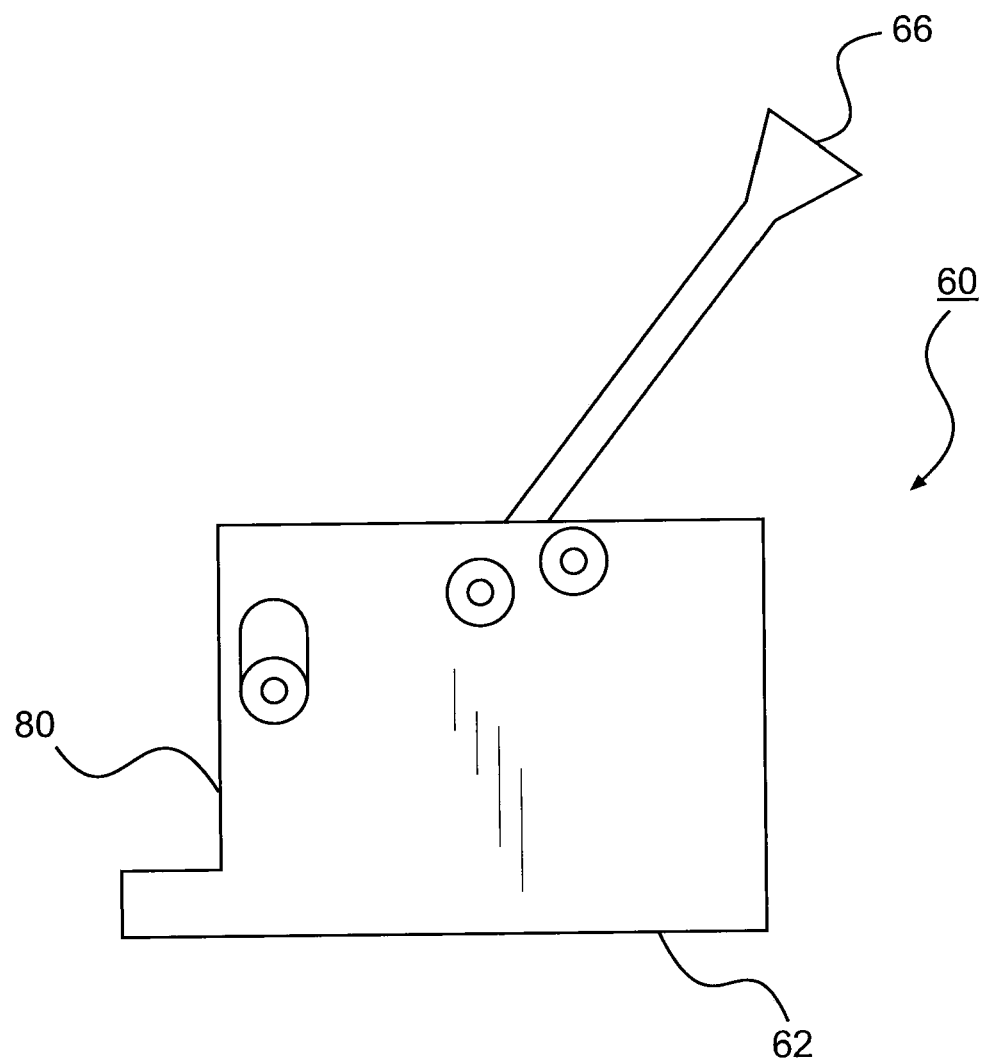
FIG. 9 illustrates a side view of the locking device.

FIGS. 6-8 show an arthroscope 22 that is adapted to be slidably received within the cannula 10. The arthroscope 22 includes a suitable knurled knob 40 having an internal threaded portion 42 in a cylindrical extension 44 and a tapered bore 46 for receiving a tubular knife or cutting blade holder 48. The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder. This will cause the tapered bore 46 of nut 40 to either compress the slotted portion 54 of the blade holder to clampingly engage the scope 50 or to loosen it so as to enable axial adjustment thereof relative to the blade holder. A regular rod-like endoscope without a blade holder may also be inserted through the cannula for effective visualization of the operative site.

FIGS. 9-12 show a locking device 60 that can be used to lock the blade holder and the transparent cannula 10 into mutually fixed positions. The locking device 60 includes a rectangular housing structure 62 with a longitudinal through bore 64 for receiving a tubular element supporting a gauge or cutting blade and for receiving a rod-like endoscope. A pivotable lever 66 mounted on the housing structure 62 is adapted to be swung between an opened position to a locked position so as to impart a clamping action to a tubular element extending through bore 64 by means of a camming structure.

Figure 10:
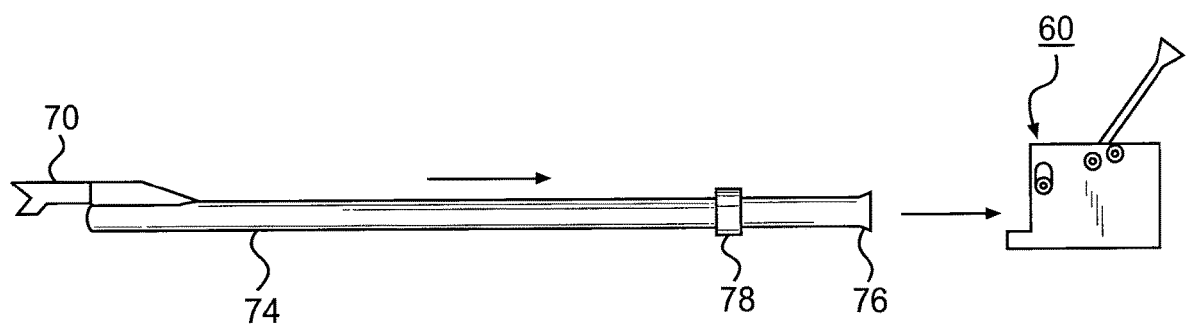
FIG. 10 illustrates a tubular member mounting a surgical knife being inserted into the locking device.

In one aspect, a cutting instrument, such as a surgical knife 70, which may be disposable, as shown in FIG. 10, is mounted at the leading end 72 of an elongate hollow tubular member 74 towards the opposite end of which the latter includes a hub portion 76 and a ring 78 spaced at a short distance therefrom, which forms a spacer defining the length of the tubular member 74 extending towards the cutting blade 70, or any cutting or rasp instrument for removing tissue, such as a "curtain" of tissue, which is provided instead of the cutting blade 70.

Figure 11:
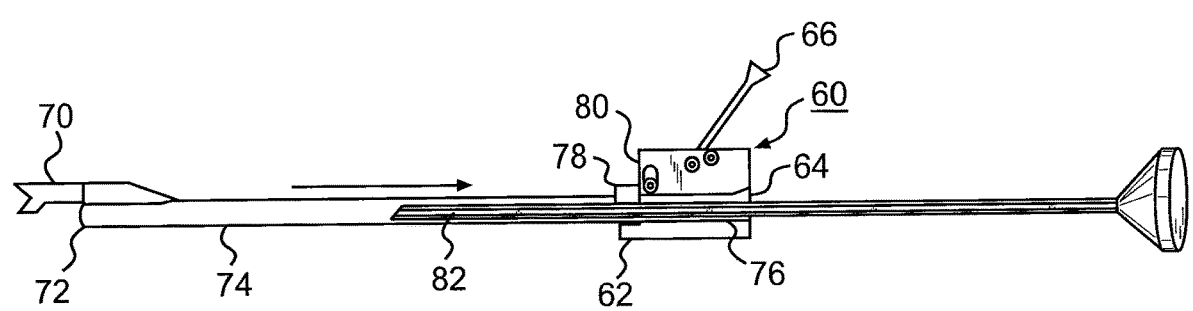
FIG. 11 illustrates the assembling of the components including an endoscope.
Figure 12:
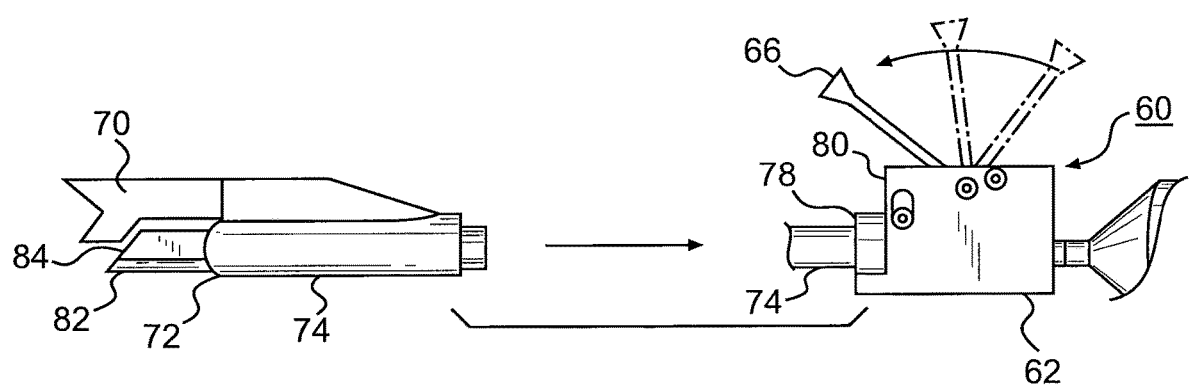
FIG. 12 also illustrates the assembling of the components including an endoscope.

As shown in FIGS. 10-12, in diagrammatic sequence, the hub end portion 76 of the hollow tubular member mounting the cutting or rasp instrument or the cutting blade 70 at the opposite end 72 is adapted to be positioned within the bore 64 formed in the locking device 60, and is inserted therein to the extent such that the spacer 78 ring which is fastened to the tubular member 74 comes into contact with the leading or forward surface 80 of the locking device 60. At that point in time, the endoscope 82 is advanced through the hollow tubular member 74 which mounts the cutting instrument or cutting blade 70, as shown in FIG. 11, and the leading end 84 of the endoscope 82 positioned closely to the cutting instrument or cutting blade 70, similar to the arrangements described in the above-mentioned U.S. Pat. Nos. 5,366,465 and 5,578,051 to Mirza.

As shown in FIG. 12, as the endoscope 82 has its leading end 84 appropriately positioned in proximity relative to the cutting instrument or cutting blade 70, the lever 66 is pivoted forwardly into the locking position, thereby causing the endoscope 82 to be clamped to the tubular member 74 mounting the cutting instrument or cutting blade 70. This will then facilitate ready insertion of the resultingly locked together components into the slotted cannula 10.

Figure 13:
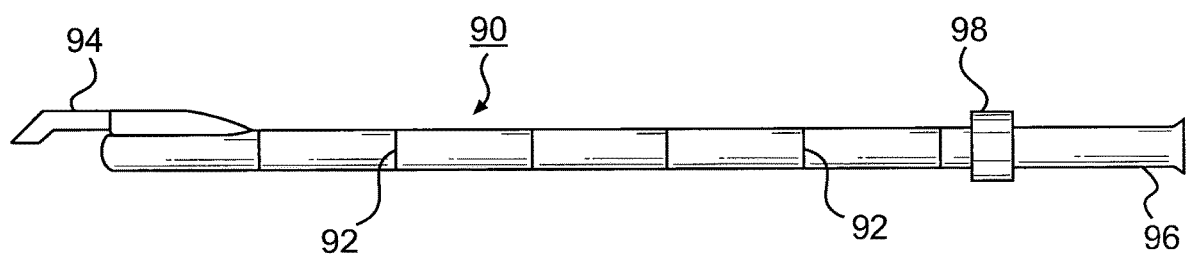
FIG. 13 illustrates the tubular member mounting a depth gauge.

The elongate tubular element 74, which mounts the knife or cutting element 70 at the leading end 72, may be calibrated along the length thereof so as to provide indication as to the depth to which the instrument is being introduced into the patient towards the surgical site. In this connection, in lieu of the tubular member mounting a knife blade or cutting element 70, prior to the use thereof with the endoscope 82, a tubular element 90 having calibrating markings 92 along the length thereof, which is similar to tubular element 74, may be equipped with a depth gauge 94 at the leading end thereof, as shown in FIG. 13, which, in a manner similar to the tubular member 74 mounting a knife or cutting element, is adapted to be inserted at the hub end 96 thereof into the locking device 60 until ring 98 contacts the locking device, with the endoscopic element inserted therein to provide illumination of the operating site, and the lever 66 being swung forwardly into the locking position.

Figure 14:
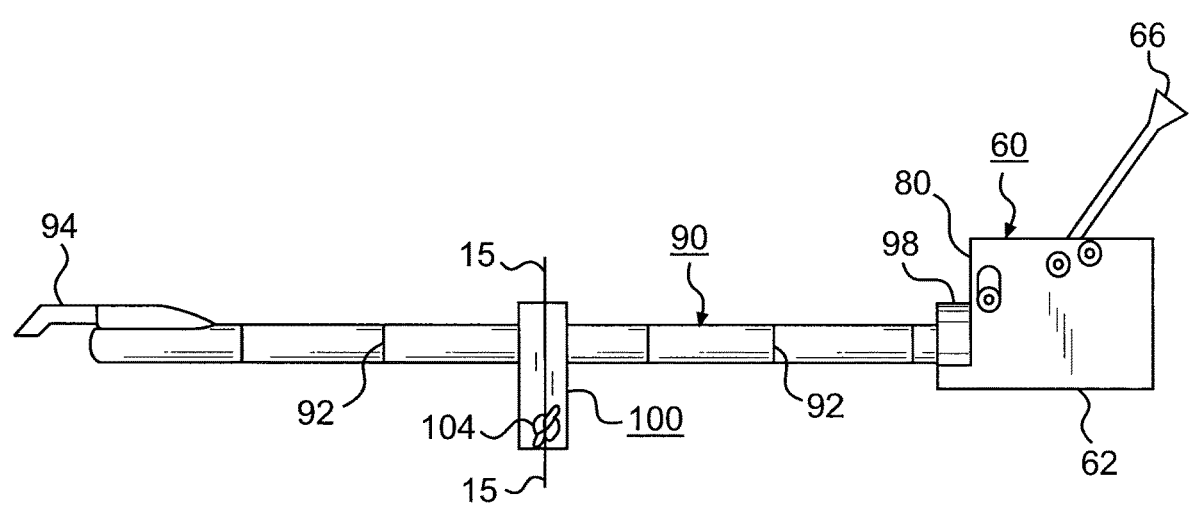
FIG. 14 illustrates the tubular member mounting the depth gauge connected to the locking device and having a stop device for limiting the extent of insertion into an incision formed in a patient.
Figure 15:
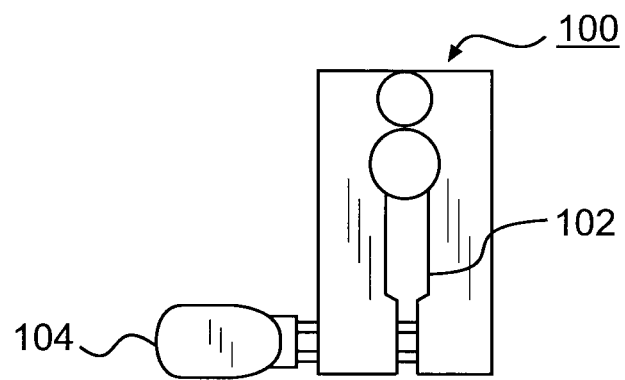
FIG. 15 is a sectional view taken along line 15-15 in FIG. 14.

Upon determination of the appropriate insertion depth to the surgical site by means of the tubular member 90 mounting the depth gauge 94, having the endoscope mounted therein, it is desirable to mount a stop device 100 in the form of a clamp member 102 on the tubular element 90 mounting the depth gauge 94, as shown in FIGS. 14 and 15, and tighten a clamping element 104, such as, for instance, a tightening screw, and which will provide information with regard to the cutting depth which is to be subsequently implemented, in that the stop device is positioned against or in proximity with the skin of the patient at the location of the incision, while the tubular element 90 and the endoscope therein are advanced within the cannula 10.

Upon withdrawing the tubular element 90 mounting the depth gauge 94 from the slotted cannula 10, a tubular element 74 mounting a knife or cutting instrument may be substituted therefore, as shown in the drawing FIGS. 10 to 12, and wherein the tubular member 74 or element mounting the knife or cutting instrument is similarly calibrated along its length. A stop device 100 is then fastened thereon at a location conforming with that of the stop device 100 which was previously mounted on the calibrated tubular member 90 mounting the depth gauge 94. This will enable the precise determination of the depth to which the cutting instrument can be inserted through the cannula 10 into the operating site, thereby preventing any injury due to any excessive penetration past the surgical site by the cutting instrument.

Figure 16:
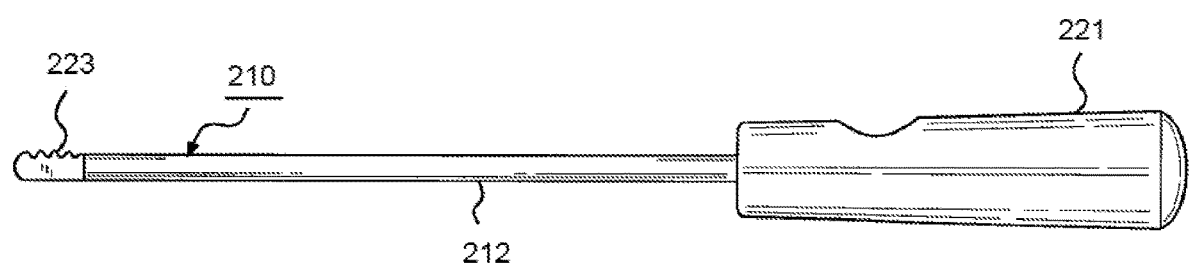
FIG. 16 illustrates a rasp member adapted to scrape a curtain of tissue at an operating site.

Furthermore, in lieu of the use of a knife blade being mounted on a tubular member 74, as the cutting element there may also be employed a unique rasp member 210 having a plurality of transverse cutting edges formed thereon, and which is adapted to scrape tissue at the operating site. FIG. 16 shows an exemplary rasp member 210 in the form of a solid rod element 212, which is insertable into the cannula 10, including a gripping end 221 and having the rasp elements 223 at the leading end thereof for advance towards the operating site. Alternatively, the rasp may comprise rasp elements mounted on a hollow tubular element similar of the type which supports the depth gauge 94 or knife 70, and is adapted to be fastened to the locking device 60 and with an endoscope passed therethrough, with the lever 66 of the locking device thereafter locking the components into mutually fixed positions.

The slotted transparent cannula and the endoscopic instruments described above may be readily applied surgical procedures such as carpal tunnel release; cubital tunnel release, plantar fascia release, lateral release for patella realignment, release of radial tunnel, release of pronatar *teres*, release of trigger finger, release of lacertous fibrosis, release of the extensor tendons for lateral epicondylitis (tennis elbow), release of medial epicondylitis (golfer's elbow), and release of fascial compartments in the upper and lower extremity. It is also possible to customize the slotted transparent cannula to adapt to other endoscopic surgical instrument for other endoscopic surgical procedures.

The transparent cannula of the present application can be inserted into the tissue through a small opening and advanced to a surgical site, thus forming a passageway towards the surgical site. The passageway allows the insertion of the endoscope and other instruments to the surgical site without further damages to the surrounding tissues. The transparent cannula body also allows endoscopic examination of the surrounding anatomical structures without any movement of the cannula body. The longitudinal slot provides improved visualization of the target anatomical structure and control over the inserted devices. The cannula is lightweight and can be produced at low cost. The slotted transparent cannula can be used in endoscopic surgical procedures such as carpal tunnel release, cubital tunnel release, plantar fascia release, lateral release for patella realignment, release of the extensor tendons for lateral epicondylitis (tennis elbow), release of the posterior and other compartments of the leg, and the forearm fascial release for fascial compartment syndrome.

Figure 17:
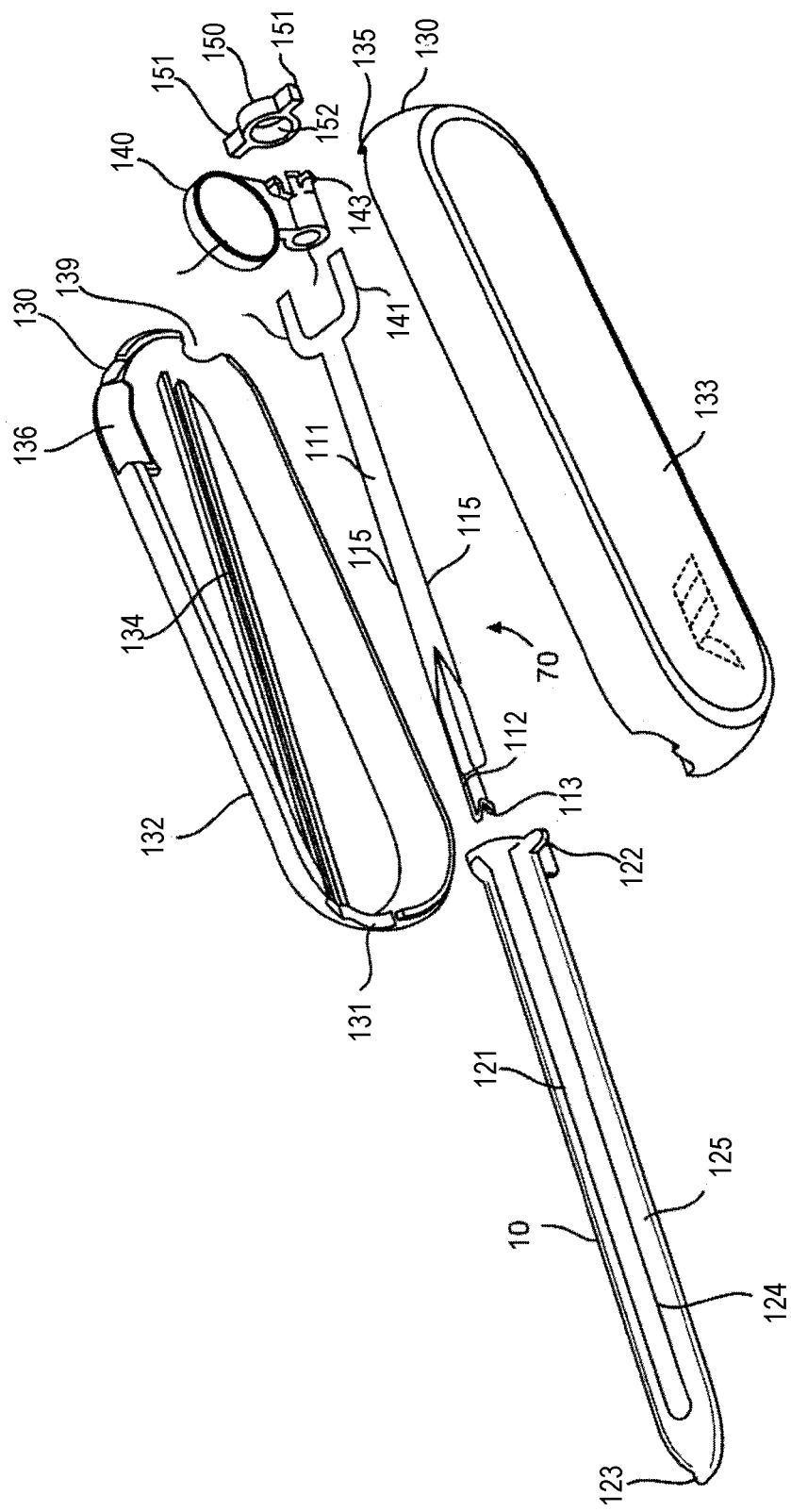
FIG. 17 is an exploded view of one embodiment of the device of the present application.

In another aspect, the present application relates to an endoscopic surgical blade assembly comprising a slotted clear cannula. In one embodiment, the surgical blade assembly comprises a linear operated device. In one exemplary embodiment depicted in FIG. 17, the device comprises a cutting blade 70, a slotted clear cannula 10, and a housing 130. The device may further include a pusher paddle 40, and may still further include a retainer ring 150.

The blade 70 comprises a horizontally-oriented pushing component 111 and a vertically-oriented cutting component 112. The cutting component 112 further comprises a sharpened cutting surface 113 at the forward end, which is the end of the blade most proximal to the cannula 10 of the device. The cutting surface 113 may be single-beveled or double-beveled.

In some embodiments, the cutting surface 113 of the blade is a single cutting surface. In some further embodiments, that single cutting surface is angled downward such that the upper end of the cutting surface is forward of the lower end of the cutting surface. In other further embodiments, that single cutting surface has a concave curve and is semi-circular or crescent shaped.

In other embodiments, the cutting surface 113 of the cutting component 112 is divided into an upper cutting surface and a lower cutting surface that are at an angle to one another and meet at a central crotch.

The design of the blade 70 is usable in endoscopic surgery in a manner that allows the practitioner to extend the blade 70 through the cannula to the target tissue without damage to surrounding tissue and/or organs. The cutting component 112 of the blade 70 is made from materials commonly used for surgical blades or scalpels, such materials include, but are not limited to, hardened and tempered steel, stainless steel, high carbon steel, titanium, alloys and ceramic.

In particular embodiments, the cutting component 112 of the blade 70 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the cutting component 112 of the blade 70 is made from Hitachi GIN-5 SST-MODIFIED 440-A stainless steel. The cutting component 112 of the blade 70 is optionally flash electropolished. The cutting edges are machine finished and must be sharp. In a particular embodiment, the steel of the cutting component 112 of the blade 70 is heat-treated to Rockwell C hardness of about 50-72. In a more particular embodiment, the steel of the cutting component 112 of the blade 70 is heat-treated to Rockwell C hardness of 58-64.

In particular embodiments, the entire blade 70 is cut from a single sheet of, or is cast from, a material commonly used for surgical blades or scalpels. The cutting component 112 is then bent into a vertical orientation that is perpendicular to the horizontal orientation of the pushing component 111. In some embodiments, the bevel(s) of the cutting surface 113 are ground prior to bending. In other embodiments, the bevel(s) of the cutting surface 113 are ground after bending.

In other embodiments, the pushing component 111 and cutting component 112 of the blade 70 are fabricated separately (by cutting or casting) and affixed to one another in their respective proper orientations. In some further embodiments, the pushing component 111 and cutting component 112 are fabricated from the same material. In other further embodiments, the pushing component 111 and cutting component 112 are fabricated from different materials, but at least the cutting component 112 is fabricated from a material commonly used for surgical blades or scalpels. In such a case, the pushing component 111 of the blade 70 may be fabricated from any suitable material providing adequate strength and rigidity for pushing the cutting component including, but not limited to, plastics, polycarbonate, hardened and tempered steel, stainless steel, high carbon steel, titanium, alloys and ceramic. Affixing of the cutting component 112 to the pushing component 111 may be accomplished by any means known in the art, such as the use of a suitable adhesive or by welding, including laser welding. In a particular embodiment, the strength of the bond between the pushing component 111 and the cutting component 112 is tested by applying torque to the unit, for example about 10 in-lbs of torque.

In particular embodiments, the blade 70 further comprises tabs 114 at the end of the pushing component 111 distal to the cutting component 112. In some embodiments, the tabs 114 extend outward to the sides of the blade 70 in the same horizontal plane as the pushing component 111, although in some embodiments, the tabs 114 may also be at an angle to that horizontal plane, as appropriate for the application. As used herein, the term "tabs" refers to either a single tab structure, two tab structures, or any other multiple as appropriate.

The tabs 114 are slidably engaged with the case or housing 30 in a manner to be further described below.

The cannula 10 is made of a clear plastic material so that the entirety of the surrounding tissue can be viewed with an endoscope. The cannula 10 is slotted along its top, with the slot 121 being contiguous with the open end 122 that is proximal to the housing 30. In some embodiments, the distal end 123 of the cannula 10 is closed, such that the cannula 10 can be inserted into a channel made through body tissue without the use of an obturator. In particular embodiments, the closed distal end 123 of the cannula is tapered, but is sufficiently blunted such that it does not damage bodily tissues as it is advanced though an incision and channel through bodily tissue, or through a natural body opening.

The cannula 10 engages with the blade 70 of the device such that the cutting component 112 inserts into and is slidably engaged with the slot 121.

In some embodiments, the cannula 10 further internally comprises horizontal blade guidance tracks 124 perpendicular to the plane of and below the slot 121. The sides 115 of the pushing component 111 of the blade 70 slidably engage with the horizontal blade guidance tracks 124, in order to allow the accurate advancement of the cutting component 112 of the blade 70 through the slot 121. In some further embodiments, the height of the horizontal blade guidance tracks 124 is level with respect to the distance from the slot 121, such that the distance the cutting surface 113 protrudes through the slot 121 is the same over the entire course of travel from the proximal end 122 of the cannula 10 to the distal end 123 of the cannula 10. In other further embodiments, the height of the horizontal blade guidance tracks 124 is at an angle with respect to the distance from the slot 121, such that the distance the cutting surface 113 protrudes through the slot 121 is lower at or near the proximal end 122 of the cannula 10 and higher at or near the distal end 123 of the cannula 10.

In some embodiments, the cannula 10 further comprises a channel 125 for the slidable insertion a viewing device, such as an endoscope. In some embodiments, the channel 125 is located below the horizontal blade guidance tracks 124. In some embodiments, the channel 125 and the horizontal blade guidance tracks 124 form a single contiguous lumen that is also contiguous with the slot 121. In other embodiments, there is a layer of material molded as part of the cannula 10 between the channel 125 and the horizontal blade guidance tracks 124, such that the lumen of the channel 125 is physically separate from the lumen contiguous with the slot 121 and comprising the horizontal blade guidance tracks 124.

In some embodiments, the proximal end 122 of the cannula 10 is adapted to engage with a connection point 131 on the front end of the housing 130. The attachment can be by any means known in the art, such as, but not limited to, adhesives, tabs, welds, laser welds, locking mechanism, twist-lock, or friction fitting. In order to provide a stable platform for endoscopic surgical procedures using the device, the attachment of the cannula 10 to the housing 130 is such that, when assembled, the cannula 10 cannot move in relation to the housing 130.

In some embodiments, the housing 130 of the device comprises two halves 132, 133 that mate to one another to form a single housing 130. In some embodiments, the housing 130 may be formed as a single piece or comprise three or more pieces.

The interior of the housing 130 comprises a guidance slot 134 on each side of the housing such that the two guidance slots 134 are horizontally opposed to one another. The tabs 114 of the blade 70 are slidably engaged with the horizontally opposed guidance slots 134. In some embodiments, the height of the horizontally opposed guidance slots 134 is parallel to with respect to a horizontal plane that would bisect the cannula 10 into two equal halves. In other embodiments, the height of the horizontally opposed guidance slots 134 is at an angle with respect to a horizontal plane that would bisect the cannula 10 into two equal halves, such that the end of the horizontally opposed guidance slots 134 distal to the cannula 10 is lower in the device with respect to the end of the horizontally opposed guidance slots 134 proximal to the cannula 10.

When the tabs 114 are drawn back in the horizontally opposed guidance slots 134, the cutting component 112 is contained within the proximate end 122 of the slot 121 of the cannula 10 and the cutting surface 113 is not protruded outside the device. As the tabs 114 are advanced in the horizontally opposed guidance slots 134 toward the connection point 131 with the cannula 10, the cutting component 112 slides in the proximate direction of the slot 121 of the cannula 10 and moves the cutting surface 113 toward the proximate end 123 of the cannula 10.

In some embodiments, the device comprises a paddle 140 that contacts the blade 70 behind or between the tabs 114. The paddle 140 comprises a grip area 141 that protrudes out of the housing 130 through a slot 135. The blade 70 is slidably advanced along the horizontally opposed guidance slots 134 by advancing the paddle 140 towards the cannula 10 through the slot 135, causing the contact area 142 of the paddle 140 to push against the pushing component 111 of the blade 70.

In some embodiments, the paddle 140 comprises at least one arm that extends forward of the tabs 114 that allows the paddle 140 to capture the tab 114 and pull the blade 70 back to a withdrawn position following completion of an endoscopic surgical procedure.

In some embodiments, the paddle 140 is secured in the device by a retaining ring 150. The retaining ring 150 comprises wings 151 that slidably interact with the horizontally opposed guidance slots 134 of the housing 130. The retaining ring 150 further comprises an attachment ring 152 that connects to the connection region 143 of the paddle 140. The connection region 143 of the paddle 140 may comprise any means known in the art for connecting the paddle 140 to the retaining ring 150. For example, the connection region 143 may comprise tabs that extend through and entrap the attachment ring 152. In some embodiments, the connection between the connection region 143 and the attachment ring 152 allows the paddle 140 to rotate side-to-side in relation to the retaining ring and the blade 70.

In some embodiments, the paddle 140 can be retained, parked or locked in a position fully distal to the cannula 10 by rotating the grip area 141 of the paddle 140 into, for example, a notch 136 in the housing 130.

In some embodiments, the housing 130 further comprises an opening 139 at the end distal to the cannula 10 through which an endoscope can be inserted. The endoscope is fed through the opening 139 and under the blade 70 to be inserted into the channel 125 of the cannula 10. This allows direct visualization of the surgical site and the surrounding tissue before, during and after performing an endoscopic surgical procedure with the present device.

Figure 18:
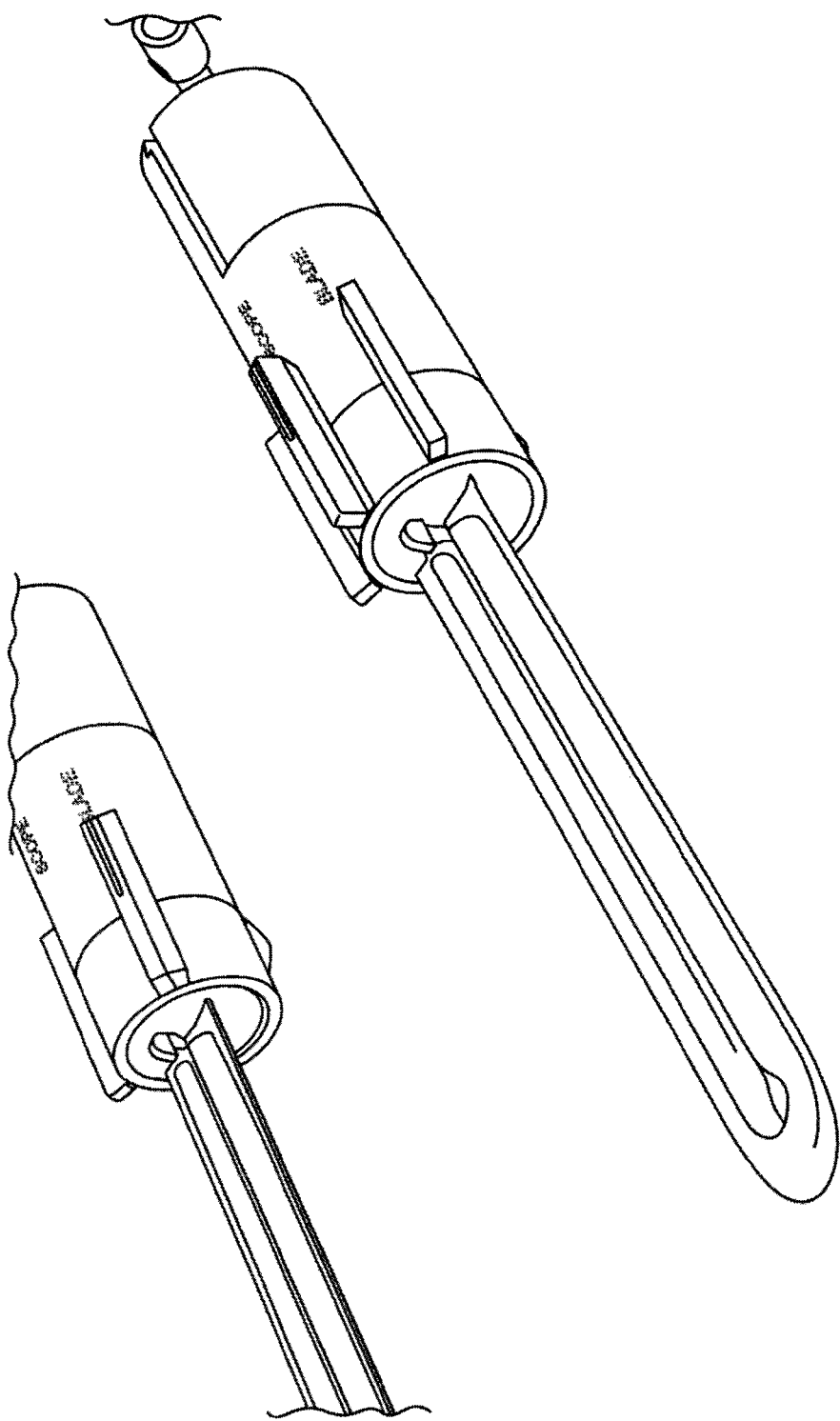
FIG. 18 is a perspective view of another embodiment of the device of the present application.

FIGS. 18 and 19 show embodiments of the present application comprising a rotationally operated device comprising a rotational switch for selecting the tool to advance into the cannula. FIG. 18 shows an embodiment comprising selection positions for advancing the endoscope alone into the cannula and for advancing a blade along the endoscope into the cannula. FIG. 19 shows an alternate embodiment, wherein the device further comprises a selectable scraper that can be advanced along the endoscope into the cannula.

Figure 20:
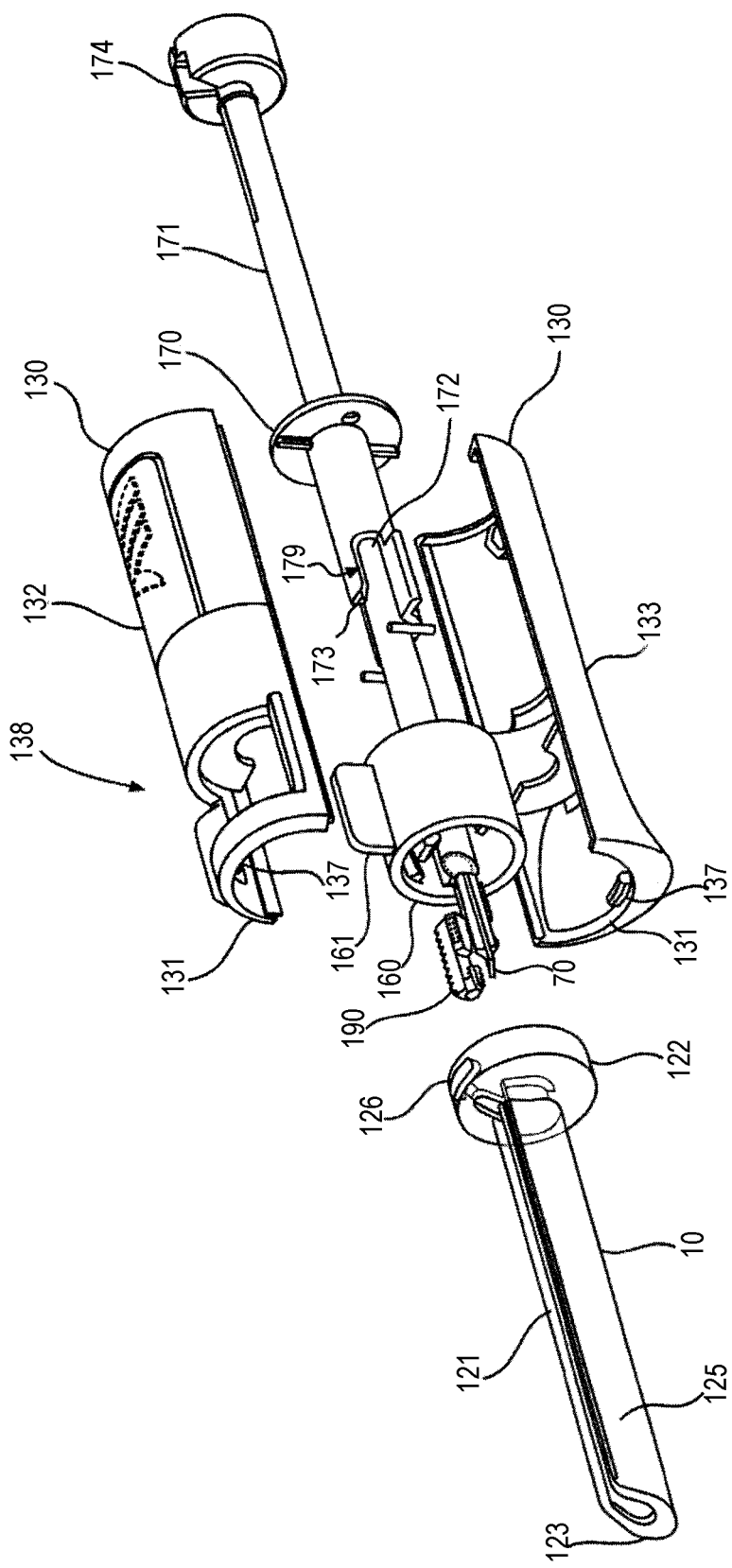
FIG. 20 is an exploded view of the embodiment of the embodiment depicted in FIG. 19.

FIG. 20 depicts an exploded view of the present device of FIG. 19. The housing 130 is cylindrical in shape and is comprised of two halves 132, 133. The proximal end 122 of the cannula 10 is adapted to engage with a connection point 131 on the front end of the housing 130. In some embodiments, the proximal end 122 of the cannula 10 comprises depressions 126 that engage with tabs (or pins) 137 at the connection point 131 on the front end of the housing 130. As used herein, the term "depression" is understood to include, but is not limited to, depressions that do not penetrate completely through the material of the cannula, as well as holes or slots that penetrate completely through the material of the cannula.

The housing 130 further includes an opening 138 that can be located in either half 132, 133 of the housing. In some embodiments, the opening 138 may span the junction between the halves 132, 133 of the housing 130, being located partially in each half. The opening 138 is located adjacent to an internal revolver 160 that comprises a selector switch 161 that protrudes through the opening 138.

Still referring to FIG. 20, the device further comprises an slide lock 170 (or inner sleeve 70) that encircles a guidance tube or tube assembly 171. The slide lock 170 comprises notches 172, 173 and a tub 179 separating the notches 172, 173, at its distal end that provide pre-deployment resting places for a cutting blade 70 and a scraper 190. The slide lock 170 works in concert with the revolver 160 in order to bring the blade 70 or scraper 190 into the proper orientation for deployment into the slot 121 of the cannula 10. The tube assembly 171 provides a path for deploying an endoscope through the device and into the cannula 10. The tube assembly 171 also provides, at its distal end, a mounting point or tube locator 178 (shown in FIG. 24A) that the cutting blade 70 or scraper 190 is rotated onto for deployment. At the proximate end of the housing, the tube assembly passes through a stabilizer ring 174, which mounts into, and seals, the proximate end of the housing. The tube assembly 171 is advanced along the deployed endoscope into the cannula 10, thereby deploying the blade 70 or scraper 190 into the slot 121 of the cannula 10.

Figure 21:
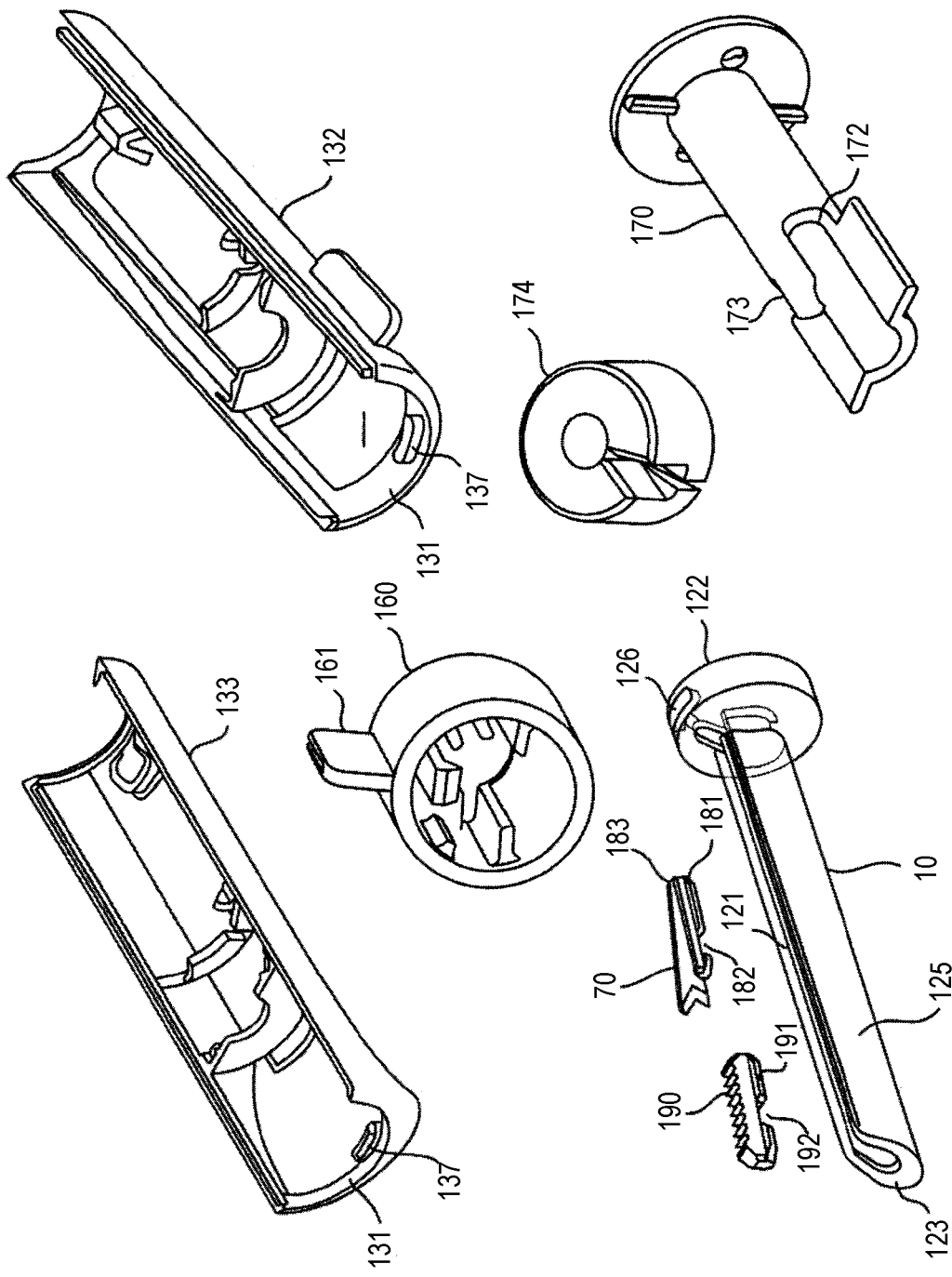
FIG. 21 shows individual components of the embodiment depicted in FIG. 19.

Turning to FIG. 21, a number of components of the device depicted in FIG. 19 are shown separately from one another. It is understood that the individual elements of the device are not limited to the exact configuration depicted in the figures herein. Any design of particular elements of the device that can be envisioned by one of ordinary skill in the art to perform the same function in concert with other elements is included as part of the present disclosure.

Also in FIG. 21, the cutting blade 70 comprises a base 181 that allows the blade 70 to be secure in its pre-deployment notch 172 of the slide lock 170. When the blade 70 is rotated into deployment orientation, the notch 182 in the base 181 engages the mounting point 178 (shown in FIG. 24A) on the distal end of the guidance tube 171. As the blade 70 is distally deployed into the slot 121 of the cannula 10, the base 181 retains the blade 70 in the device by underlapping the sides of the slot 121 within the channel 125 of the cannula 10. Additionally, to prevent any unwanted side-to-side motion of the blade 70 as it is deployed distally through the slot 121 of the cannula 10, in some embodiments the blade further comprises a ridge 183 that fills the slot side-to-side. Additionally, the engagement of the notch 182 with the mounting point 178 allows the cutting blade 70 to be safely retracted back into the housing 130 following usage of the blade 70 for an endoscopic surgical procedure.

Still referring to FIG. 21, the scraper 190 comprises a base 191 that allows the scraper 190 to be secure in its pre-deployment notch 173 of the slide lock 170. When the scraper 190 is rotated into deployment orientation, the notch 192 in the base 191 engages the mounting point 178 (shown in FIG. 24A) on the distal end of the guidance tube 171. As the scraper 190 is distally deployed into the slot 121 of the cannula 10, the base 191 retains the scraper 190 in the device by underlapping the sides of the slot 121 within the channel 125 of the cannula 10. Additionally, the engagement of the notch 192 with the mounting point 178 allows the scraper 190 to be safely retracted back into the housing 130 following usage of the scraper 190 for an endoscopic surgical procedure.

Figure 22:
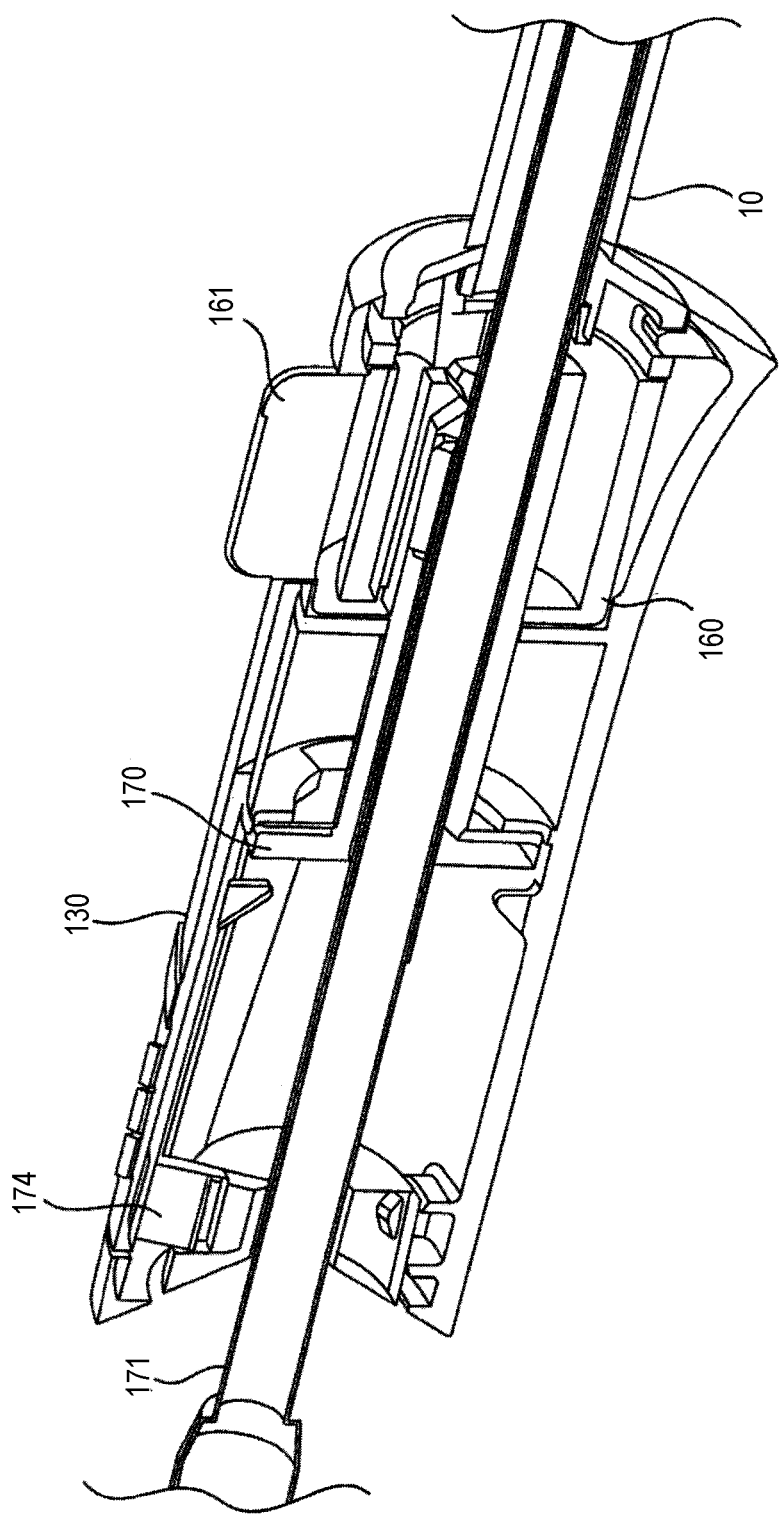
FIG. 22 is a cutaway view of the embodiment of the embodiment depicted in FIG. 19.

Turning to FIG. 22, a cutaway drawing is shown that depicts the passage of the guidance tube or tube assembly 171 through the slide lock 170 and into the cannula 10.

Figure 23:
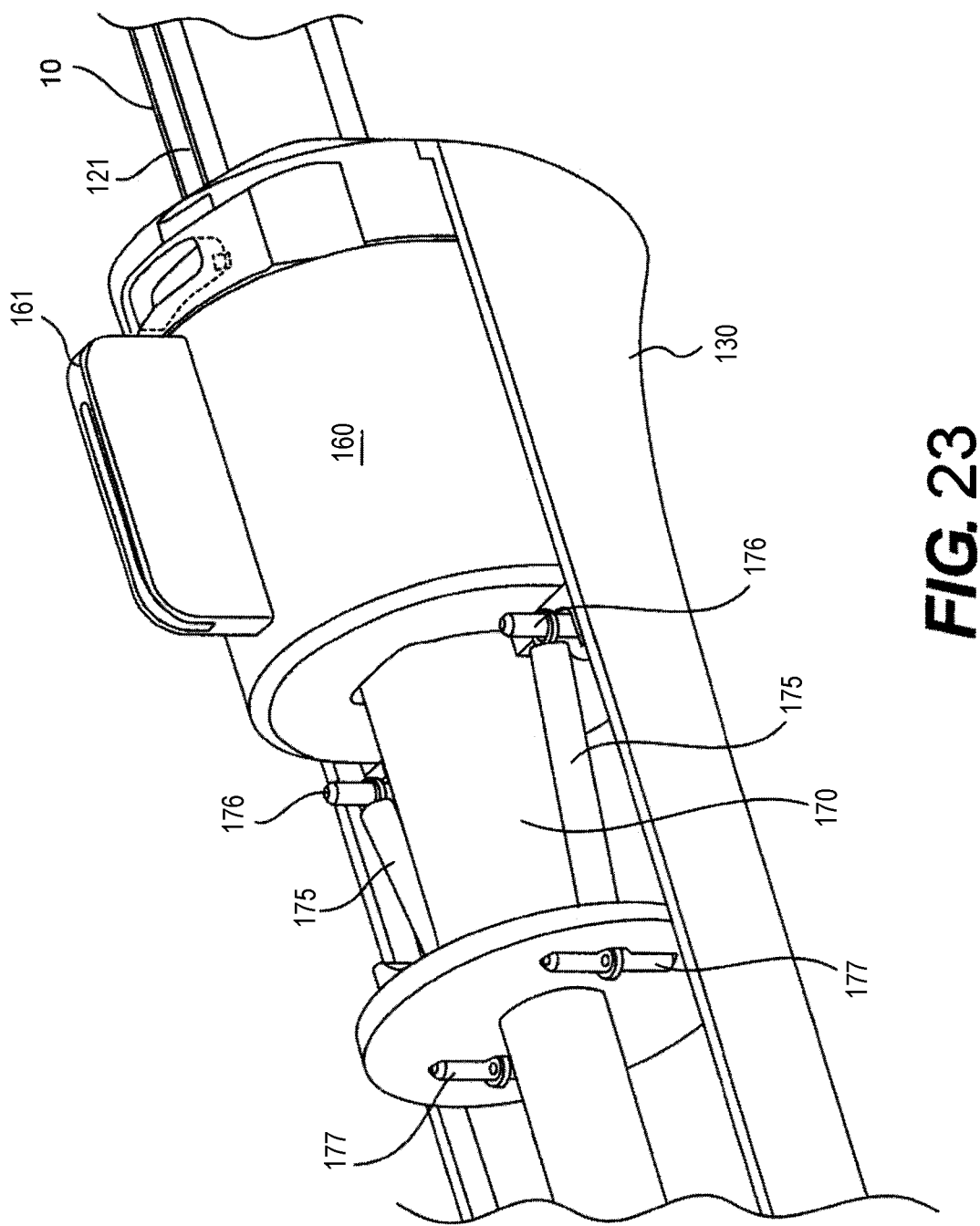
FIG. 23 is an exploded view of individual components of the embodiment depicted in FIG. 19.

FIG. 23 is a cutaway drawing showing an exemplary relationship of the slide lock 170 to the revolver 160 of the device. The slide lock 170 extends into the revolver 160 and the pre-deployment slots 172, 173 holding the blade 70 and the scraper 190 are located inside the revolver 160. In an exemplary configuration, springs 175 are attached to pins 176 located on the revolver 160. The springs 175 extend to pins 177 that secure the opposite end of the springs to the slide lock 170. The springs 175 auto center the revolver 160 within the device. Upon rotation of the revolver 160, the springs 175 activate detents for the three modes: 1) deployment of the endoscope, 2) orientation of the scraper 90 in deployment configuration, and 3) orientation of the blade 70 in deployment configuration.

Figure 24A:
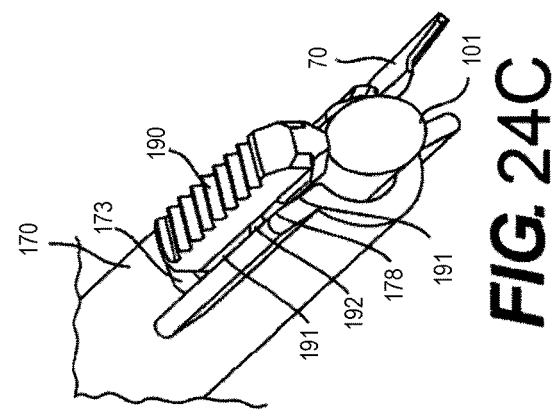
FIGS. 24A-F show the orientation of the internal components in side view (A, C.
Figure 24B:
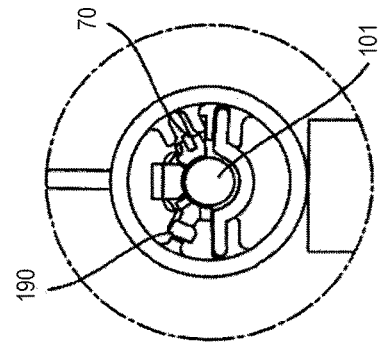

FIGS. 24A-F show the rotation of the slide lock corresponding to the three modes. FIG. 24A, viewing from above, and 24B, viewing from a distal position, depicts a first mode, wherein an endoscope 101 is advanced through the guidance tube 171 into the cannula 10, without the deployment of the scraper 190 or the cutting blade 70. The mounting point 178 is not engaged with either the blade 70 or the scraper 190, therefore preventing the deployment of either tool in this mode.

Figure 24C:
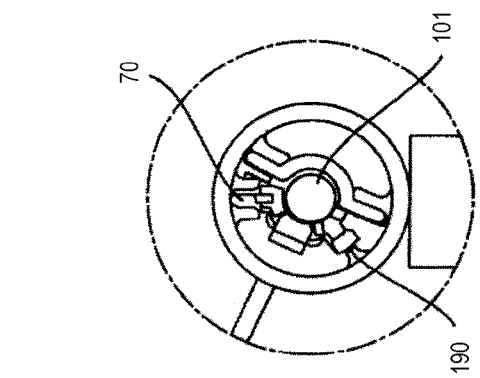
Figure 24D:
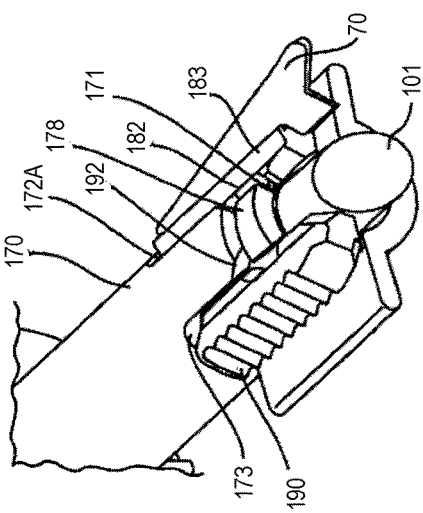

FIG. 24C, viewing from above, and 24D, viewing from a distal position, depict a second mode, wherein the revolver 160 has been turned to select the scraper 190. The slide lock 170 is rotated in concert with the revolver 160 to bring the scraper 190 into deployment orientation. The slot 192 in the base 191 of the scraper 190 is rotated to engage the mounting point 178 on the guiding tube (hidden). The guiding tube is then pushed distally into the cannula 10 with the scraper 190 protruding through the slot 121. Following use of the scraper 190, the guiding tube is retracted from the cannula 10 and the revolver 160 is returned to the first mode, restoring the scraper to its pre-deployment configuration of FIGS. 24A-B.

Figure 24E:
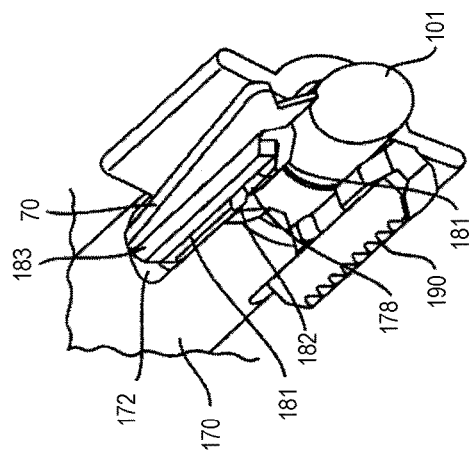
Figure 24F:
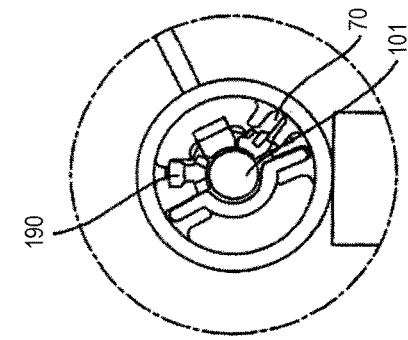

FIG. 24E, viewing from above, and 24F, viewing from a distal position, are a depiction of the third mode, wherein the revolver 160 has been turned to select the blade 70. The slide lock 170 is rotated in concert with the revolver 160 to bring the blade 70 into deployment orientation. The slot 182 in the base 181 of the blade 70 is rotated to engage the mounting point 178 on the guiding tube (hidden). The guiding tube is then pushed distally into the cannula 10 with the blade 70 protruding through the slot 121. Following use of the blade 70, the guiding tube is retracted from the cannula 10 and the revolver 160 is returned to the first mode, restoring the blade 70 to its pre-deployment configuration of FIGS. 24A-B.

FIG. 25 is a perspective view from above an embodiment of the device showing, in particular, the cannula 10, housing 130 and tube assembly 171 as they appear in the assembled device prior to deployment of the tube assembly 171 into the cannula 10 with the scraper tool or blade assembly.

FIG. 26 is an exploded view of the embodiment of the device shown in FIG. 25. FIG. 26 shows the cannula 10 which joins to the distal end of top half 132 and bottom half 133 of the housing 130. Interior to the housing 130 is the revolver 160, having a selector switch 161 for choosing the "BLADE," "SCOPE," or "SCRAPER" position of the slide lock 170, which is positioned inside the revolver 160. The blade 70 and scraper 190 tools are parked in notches 172, 173 in the slide lock 170 and are retained there when not deployed by a rotary clip 270. The tube assembly 171 passes through the slide lock 170 within the housing 130. The distal end of the tube assembly 171 extends and is deployable into the cannula 10. The tube assembly 171 comprises near its distal end a tube locator 178 that the blade 70 or scraper 190 tool is engaged with for deployment into the cannula 10. The tube assembly 171 further comprises, at its proximate end, a tube stop 184 that prevents the proximate end of the tube assembly 171 from passing through the stabilizer ring 174 mounted in the rear of the housing 130. The tube assembly 171 has a longitudinal central lumen that accommodates the insertion of an endoscope through the tube assembly 171 and into the clear cannula 10 in order to visualize the tissue surrounding the cannula 10 and to observe the surgical procedure performed with the compact endoscopic surgical device. In some embodiments, the tube stop 184 is gripped by the practitioner or engaged to a grippable attachment 300 (FIG. 25) to allow the tube assembly to be operated manually for advancement or withdrawal of the tube assembly 171. In other embodiments, the tube stop 184 is engaged to an apparatus or machine for automatic or remote control of advancement or withdrawal of the tube assembly 171.

FIGS. 27A-E show details of the clear cannula element of the device. FIG. 27A shows the cannula 10 from the top, showing the slot 121 extending longitudinally from the proximity of the proximal end 122 to the proximity of the distal end 123. Also visible are the depressions, slots, or holes 126 that engage with tabs or pins on the front of the housing. In some embodiments, the sides of the slot 121 comprise texture or tick marks 127 that are at a measured distance from one another down the length of the slot 121. The tick marks 127 minimally engage with the carrier of the blade and/or scraper as it advances, or retreats, along the length of the slot 121 to allow the practitioner to feel, or otherwise determine, how far the carrier has advanced along the slot. In some embodiments, the distal end 123 of the cannula 10 is blunted and serves as an obturator.

FIG. 27B shows a side view of the cannula 10, showing the proximate 122 and distal 123 ends, as well as the depressions, slots, or holes 126 that engage with tabs or pins on the front of the housing. In some embodiments, the distal end 123 of the cannula is angled upwards, as an obturator.

FIG. 27C depicts an angled view of the clear cannula 10 of the device. In some embodiments, the depressions, slots, or holes 126 that engage with tabs or pins on the front of the housing are located on the top and bottom of the proximate end 122 of the cannula 10. In some embodiments, rather than individual or multiple depressions, slots, or holes 126 on the top, bottom or sides of the cannula 10, the depression 126 may be an impression or groove that runs all the way around the outside of the proximate end 122 of the cannula 10 and engages with an annular ring that runs around the inside of the distal end of the housing.

FIG. 27D shows an end view of the cannula at the proximate end 122. The view shows the slot, which is contiguous with the central lumen 128 of the cannula. FIG. 27E is a cross-sectional view of the cannula 10 at bisecting line E-E in FIG. 27A, looking towards the proximate end of the cannula 10. The longitudinal slot 121 in the top surface of the cannula 10 can be seen to be contiguous with the central lumen of the cannula tube 10.

FIGS. 28A-F show various views of the top half 132 of the housing 130. FIG. 28A shows the outside of one embodiment of the top half 132 of the housing 130 at an angle, while FIG. 28B shows the inside of one embodiment of the top half 132 of the housing 130 at an angle. FIG. 28C shows the inside of one embodiment of the top half 132 of the housing 130, showing one embodiment of a tab or pin 137 that engages with a depression, slot, or hole located on the proximate end of the cannula shown in FIGS. 27A-E. In some embodiments, rather than individual or multiple tabs or pins at the distal end of the housing, the tab 137 may be an annular ring that runs around the inside of the distal end of the housing 130 and engages an impression or groove that runs all the way around the outside of the proximate end of the cannula. FIG. 28D shows the upper half 132 of the housing 130 from a side view, while FIG. 28E shows a view of the top half 132 of the housing 130 from the distal end and FIG. 28F shows a view of the top half 132 of the housing 130 from the proximate end.

Figure 29D:
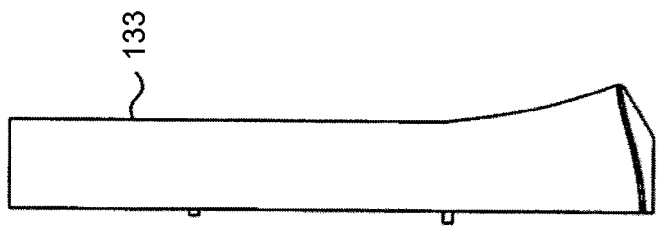
Figure 29C:
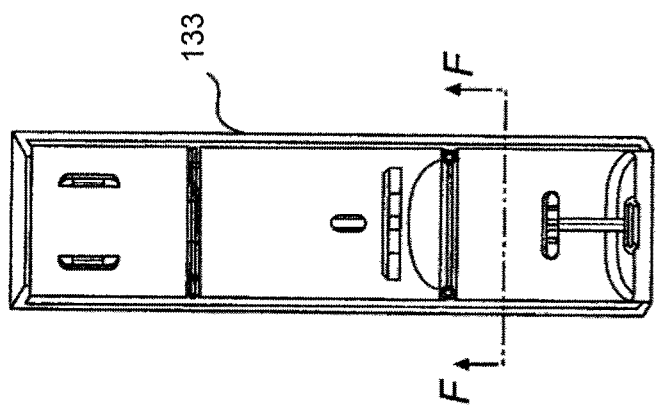
Figure 29F:
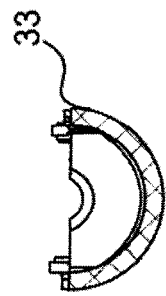
Figure 29B:
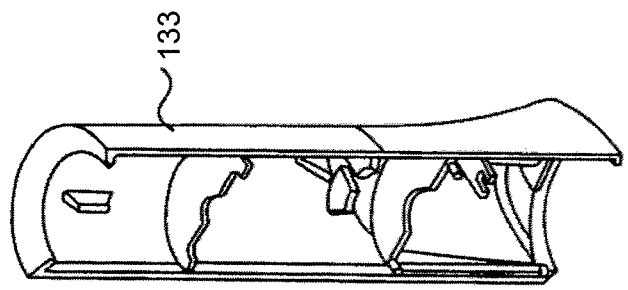
Figure 29E:
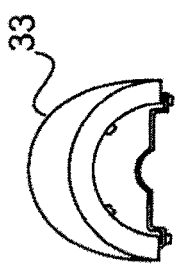
Figure 29A:
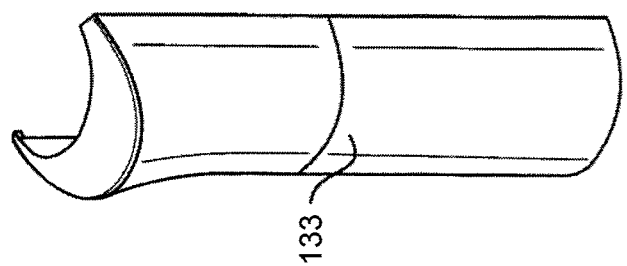

FIGS. 29A-F show various views of the lower half 133 of the housing 130. FIG. 29A shows the outside of one embodiment of the lower half 133 of the housing 130 at an angle, while FIG. 29B shows the inside of one embodiment of the lower half 133 of the housing 130 at an angle. FIG. 29C shows the inside of one embodiment of the lower half 133 of the housing 130. FIG. 29D shows the lower half 133 of the housing 130 from a side view, while FIG. 29E shows a view of the lower half 133 of the housing 130 from the distal end and FIG. 29F shows a cross-sectional view looking towards the distal end of the lower half 133 of the housing 130 from the line A-A bisecting FIG. 29C.

Kit

Another aspect of the present invention relates to an instrument kit for implementing an endoscopic surgical procedure. The instrument kit contains a transparent cannula guide member including a longitudinal bore having open proximal and distal ends and an open slot extending along the length thereof communicating with the open ends, and an elongate insertion member that is slidably receivable within the cannula guide member and is configured so that at least portions thereof conform with the open distal end and the open slot of the guide member to form a smooth exterior surface in combination therewith.

In another embodiment, the instrument kit includes an endoscopic surgical blade assembly, including a slotted clear cannula, a blade and a housing, wherein the cannula is attached to the housing, and further wherein the blade is enclosed in the housing and is slidable into the cannula. In a particular embodiment, the endoscopic surgical blade assembly includes a slotted clear cannula, a scraper, a blade and a housing, wherein the cannula is attached to the housing. In a pre-deployment configuration, the scraper and the blade are enclosed in the housing, the blade and scraper are individually selectable for deployment orientation, and the blade or scraper is slidable into the cannula in a deployment orientation.

In some embodiments, the instrument kit further includes an endoscope sized for insertion into the cannula guide member for direct visualization of an operative site.

In other embodiments, the instrument kit further includes a knife configured for slidable movement through the cannula guide member.

In one embodiment, the endoscope carries a cutting instrument at a leading end.

In another embodiment, the instrument kit further includes a cutting instrument mountable to the leading end of the endoscope.

In another embodiment, the instrument kit further includes a second endoscope with a cutting instrument mounted at a leading end of the second endoscope. The second endoscope is insertable into the cannula guide member such that the cutting instrument protrudes through the open slot in the cannula guide member.

In another embodiment, the instrument kit further includes a scalpel.

In another embodiment, the instrument kit further includes a ligament probe

In one embodiment, the instrument kit further includes a depth gauge mountable to a leading end of the endoscope.

In another embodiment, the instrument kit further includes a rasp member sized for insertion into the cannula guide member.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument.

In another embodiment, the instrument kit further includes a curved dissector.

In another embodiment, the instrument kit further includes an elevator.

Method for Endoscopic Surgery

Another aspect of the present invention relates to a method for implementing a uniportal endoscopic surgical procedure using the slotted transparent cannula of the present invention. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The transparent cannula of the present invention can be inserted into the tissue through a small opening proximate to a target tissue and advanced to the target tissue, thus forming a passageway towards the target tissue. The insertion site can be on the proximal or distal side of the target tissue. The passageway allows the insertion of the endoscope and other instruments to the target tissue without further damages to the surrounding tissues. The transparent cannula body also allows endoscopic examination of the surrounding anatomical structures without any movement of the cannula body. The longitudinal slot provides improved visualization of the target anatomical structure and control over the inserted devices. The cannula is lightweight and can be produced at low cost.

In one embodiment, an endoscopic surgical device includes a slotted clear cannula, a blade and a housing, wherein the cannula is attached to the housing, and further wherein the blade is enclosed in the housing and is slidable into the cannula, is inserted into the entry portal and extended through to the target tissue.

In some embodiments, the cannula is attached to the housing, in a pre-deployment configuration the scraper and the blade are enclosed in the housing, the blade and scraper are individually selectable for deployment orientation, and in deployment orientation the blade or scraper are slidable into the cannula. In some further embodiments, the device comprises a tube assembly that allows a viewing device to be inserted through a central lumen, wherein the tube assembly engages separately with the blade or the scraper and advancing the tube assembly into the slotted clear cannula advances the selected blade or scraper.

In some embodiments, the endoscopic surgical device further comprises a mechanism for locking the viewing device in a fixed position relative to the tube assembly. In some further embodiments, the scope lock assembly engages with the tube assembly and is used as a handle for advancing or withdrawing the tube assembly into or from the slotted clear cannula.

An endoscope may be inserted through the housing and into the cannula to view the target tissue and the surrounding tissues, assuring that the slot of the cannula is in proper orientation to the target tissue.

In one particular embodiment, the operative procedure is trigger finger release.

In another particular embodiment, the target tissue is the A1 pulley.

In one embodiment, the method includes the steps of making an incision on a patient in need of such endoscopic surgical procedure at a location proximate an operation site (or target tissue) to establish an entry portal, inserting the distal end of the transparent cannula into the incision; advancing the distal end of the transparent cannula to the operation site; inserting an endoscope into the transparent cannula for direct visualization of anatomic structures surrounding the transparent cannula and positioning of the transparent cannula at the operative site; inserting a cutting instrument into the transparent cannula such that the cutting instrument protrudes into an open slot in the transparent cannula, and operatively engaging the target tissue with the cutting instrument under direct visualization of the endoscope so as to perform a desired operative procedure on the target tissue; withdrawing the cutting instrument from the transparent cannula; withdrawing the transparent cannula through the entry portal; and suturing the incision.

In some embodiments, the entry portal is established proximal to the operation site or the target tissue. In some embodiments, the entry portal is established distal to the operation site or the target tissue. In some embodiments, the target tissue is divided or cut by advancing the cutting instrument towards the distal end of the clear cannula. In other embodiments, the cutting instrument comprises a hooked blade and the target tissue is divided or cut by pulling the cutting instrument towards the proximal end of the clear cannula.

The uniportal endoscopic surgical procedure described herein can be used to implement a number of different surgical procedures including, but not limited to, carpal tunnel release, cubital tunnel release, plantar fascia release, lateral release for patella realignment, release of radial tunnel, release of pronatar *teres*, release of trigger finger, release of lacertus fibrosus, Guyon's canal (or canal) release, release of the extensor tendons for lateral epicondylitis (tennis elbow), release of the medial epicondylitis, release of the posterior and other compartments of the leg, forearm fascia release for fascial compartment syndrome, release of fascial compartments in the upper or lower extremities, relieving the compression of a nerve by a ligament pulley or tunnel, releasing the travel of a ligament through a ligament pulley or tunnel, surgical procedures on the spine, such as endoscopic discectomy for the treatment of degenerative disc disease, herniated discs, bulging discs, pinched nerves or sciatica, endoscopic procedures on cranial and facial tissues, fasciotomy release and blood vessel harvesting.

The present invention is further illustrated by the following examples which should not be construed as limiting. The contents of all references, patents and published patent applications cited throughout this application, as well as the Figures, are incorporated herein by reference.

Example 1: Use of the Slotted Transparent Cannula (Hereinafter "Clear Cannula") for Endoscopic Carpal Tunnel Release Introduction of Clear Cannula A single incision is made in the palm, proximal or distal to the transverse carpal ligament (TCL). A curved dissector is inserted to form a passage beneath the TCL. Once the pathway is created and the dissector removed, the Clear Cannula are introduced into the same pathway. The cannula tip should always stay against the under surface of the TCL and superficial to the flexor tendons and ulnar bursa. Rotate the assembly so the slot of the cannula faces slightly toward the ulnar side. The cannula should not be rotated past two and ten o'clock respectively.

Endoscopic Visualization of Anatomy

A 4 mm, 30 degree endoscope, oriented towards the slot of the cannula, is then introduced into the cannula. Visualization of the transverse carpal ligament fibers and fibers of the antebrachial fascia should be visible through the slotted portion of the cannula. If the transverse fibers of the TCL are not clearly seen, the cannula must be removed and the introduction procedure repeated.

The Clear Cannula should allow for adequate visualization of the median nerve and flexor tendons without the need to rotate the slot of the cannula towards these anatomic structures. Due to variations of anatomy, visual confirmation of these structures may not be possible. If visualization of these structures is inadequate, the surgeon may rotate the slot of the cannula towards the median nerve (radial) and flexor tendons (ulnar) to verify proper cannula placement.

Division of the Transverse Carpal Ligament

With a clear view of the transverse fibers of the TCL and no other intervening structures visible within the slotted portion of the cannula, a cutting tool is introduced into the cannula and, as the surgeon observes the monitor, the TCL is divided by engaging the cutting surface of the cutting tool with the TCL and then advancing the cutting tool towards the distal end of the clear cannula (for cutting tools with a forward facing cutting surface) or pulling the cutting tool back towards the proximal end of the cannula (for cutting tools with a backward facing cutting surface).

Once division is complete, remove the cutting tool from the cannula, and remove the Clear Cannula from the operation site.

This procedure dramatically reduces the risk of damaging any tissue and nerves, such as the median nerve, in the vicinity of the operating site. It also enables the surgeon to exercise an improved degree of control over the possibly single-handed manipulation of the endoscopic instrument and cutting blade.

Example 2: Use of the Clear Cannula for Endoscopic Cubital Tunnel Release Introduction of the Clear Cannula An "X" is placed on both the medial epicondyle and olecmon. A 3-4 cm incision is made along the course of the ulnar nerve at the cubital tunnel between the marked anatomical structures. A dissector is inserted to form a passage beneath the distal and proximal ulnar sheath. Once the distal or proximal pathway is created and the dissector removed, introduce the Clear Cannula into the same pathway. The surgeon should have direct visualization of the ulnar nerve so that the slotted portion of the cannula can be positioned 180 degrees to the ulnar nerve.

2-c. Endoscopic Visualization of Anatomy

A 4 mm, 30 degree endoscope, oriented towards the slot of the cannula, is then introduced into the cannula. Visualization of the (distal/proximal) ulnar nerve sheath should be visible through the slotted portion of the cannula. If the transverse fibers of the fascia are not clearly seen, the cannula must be removed and the introduction procedure repeated.

The Clear Cannula should allow for adequate visualization of the ulnar nerve and surrounding tissue without the need to rotate the slot of the cannula towards these anatomic structures. Due to variations of anatomy, visual confirmation of the ulnar nerve may not be possible. If visualization is inadequate, the surgeon may rotate the slot of the cannula towards the ulnar nerve to verify proper cannula placement.

Division of the Distal and Proximal Ulnar Sheath

With a clear view of the transverse fibers of distal/proximal ulnar sheath and no other intervening structures visible within the slotted portion of the cannula, a cutting tool is introduced into the cannula and, as the surgeon observes the monitor, the TCL is divided by engaging the cutting surface of the cutting tool with the TCL and then advancing the cutting tool towards the distal end of the clear cannula (for cutting tools with a forward facing cutting surface) or pulling the cutting tool back towards the proximal end of the cannula (for cutting tools with a backward facing cutting surface).

Once division is complete, remove the cutting tool from the cannula, and remove the Clear Cannula from the operation site.

Example 3: Uniportal Endoscopic Carpal Tunnel Release

In a patient presenting with carpal tunnel syndrome, an incision is made just proximal or distal to the carpal transverse ligament.

An endoscopic viewing device is inserted into an endoscopic surgical device having a slotted clear cannula that comprises a sharpened front edge for separating tissues. The viewing device is advanced into a tube assembly that can be engaged in the device with a blade or scraper and locked in place in relation to the tube assembly. The revolver of the device is set to allow the advancement of the tube assembly and endoscope without the deployment of the blade or scraper and the tube assembly is advanced into the cannula and locked into place.

The slotted clear cannula having a sharpened front edge is introduced into the incision and used to create a plane under the carpal transverse ligament, but superficial to the median nerve, with the slot of the cannula facing the carpal transverse ligament. The procedure is observed with the viewing device.

Following the creation of the plane, the tube assembly, still with the viewing device locked in place in relation to the tube assembly, is withdrawn back into the housing of the device. In the event that the ligament sheath obscures visualization of the ligament, the revolver of the device is turned to select deployment orientation of the scraper. The tube assembly is advanced into the cannula and the scraper protrudes through the slot of the cannula. The ligament sheath is removed with the scraper and the tube assembly is retracted, bringing the scraper back into the housing of the device. The revolver of the device is rotated to restore the scraper back to its pre-deployment configuration in the device.

The ligament is again visualized with the endoscope, the tube assembly is retracted and the revolver of the device is turned to select deployment orientation of the blade. The tube assembly is advanced with the endoscope into the cannula and the blade protrudes through the slot of the cannula. The blade is advanced into contact with the carpal transverse ligament. The blade is further pushed forward, dividing the carpal transverse ligament. The tube assembly is retracted, bringing the blade back into the housing of the device. The revolver of the device is rotated to restore the blade back to its pre-deployment configuration in the device.

The cut edges of the carpal transverse ligament and the underlying median nerve and tendons attached to the digits are visualized through the endoscope.

While visualizing the nerve and tendons, release is confirmed by passive manipulation of the digits through their range of motion.

The cannula is removed from the incision.

The wound is closed and a soft bandage is applied. In some cases, a splint is also applied to immobilize the wrist up to a week.

Example 4: Uniportal Endoscopic Trigger Release

In a patient presenting with trigger finger of the middle or ring finger, an incision is made just proximal to the A1 pulley on the distal palmar crease proximate to the affected digit or distal to the A1 pulley at or near the base of the affected digit.

An endoscopic viewing device is inserted into a slotted clear cannula having a sharpened front edge. The cannula is introduced into the incision and the sharpened front edge is used to create a plane superficial to the flexor tendon sheath, with the slot of the cannula facing the flexor tendon sheath. The procedure is observed with the viewing device.

In the event that the tenosynovium obscures visualization of the tendon, a scraper is advanced into the cannula and protrudes through the slot of the cannula. The tenosynovium is removed with the scraper and the scraper is retracted.

The flexor tendon sheath and the surrounding tissues are again visualized with the endoscope. A blade is advanced into the cannula and protrudes through the slot of the cannula. The blade is advanced into contact with the flexor tendon sheath. The blade is further pushed forward, dividing the flexor tendon sheath. The blade is retracted.

The cut edges of the flexor tendon sheath and the underlying flexor tendon are visualized through the endoscope. While visualizing the tendon, release of the tendon is confirmed by passive manipulation of the digit through its range of motion.

Example 5: Uniportal Endoscopic Cubital Tunnel Release

A patient presenting with a persistent tingling or "pins and needles" sensation in the hand, particularly in the ring and little fingers. The patient is diagnosed with cubital tunnel syndrome, having ulnar nerve entrapment through the cubital tunnel by the tendinous arch joining the humeral and ulnar heads of the flexor carpi ulnaris and/or the fascia tissue forming the tunnel. The patient is referred for surgical release of the tunnel. An incision is made directly over the ulnar nerve between the medial epicondyle and the olecranon.

An endoscopic viewing device is inserted into an endoscopic surgical device having a slotted clear cannula that comprises a sharpened front edge for separating tissues. The viewing device is advanced into a tube assembly that can be engaged in the device with a blade or scraper and locked in place in relation to the tube assembly. The revolver of the device is set to allow the advancement of the tube assembly and endoscope without the deployment of the blade or scraper and the tube assembly is advanced into the cannula and locked into place.

The slotted clear cannula having a sharpened front edge is introduced into the incision in the distal direction (i.e., towards the hand) and used to create a plane under the tendinous arch and fascia, but superficial to the ulnar nerve, with the slot of the cannula facing the tendinous arch and fascia. The procedure is observed with the viewing device.

The tube assembly is retracted from the cannula, back into the device, and the revolver of the device is turned to select deployment orientation of the blade. The tube assembly is advanced with the endoscope into the cannula and the blade protrudes through the slot of the cannula. The blade is advanced into contact with the tendinous arch and fascia of the tunnel to the distal side of the incision. The blade is further pushed forward, dividing the arch and fascia. The tube assembly is retracted, bringing the blade back into the housing of the device. The revolver of the device is rotated to restore the blade back to its pre-deployment configuration in the device.

The cut edges of the arch and fascia and the underlying ulnar nerve may be re-visualized through the endoscope.

The cannula is removed from the incision. In some instances, the fascia proximal to the incision may also need to be released. The cannula is re-inserted into the incision, this time in the proximal direction (i.e., towards the shoulder) and the viewing and division procedures are repeated, if necessary.

Before the skin is closed, the elbow is taken through its range of motion and the ulnar nerve is visualized through the incision to confirm that there is no subluxation of the ulnar nerve. The wound is closed and a soft bandage is applied. Early range of motion are started as soon as the patient can tolerate them and the patient is encouraged to resume activities as soon as they are comfortable.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A device for an endoscopic surgical procedure, comprising:
    (a) a housing having a proximate end and a distal end;
    (b) a slotted clear cannula attached to the distal end of the housing, the slotted clear cannula comprising a cannula body having a proximate end and a distal end, and a slot extending from the proximate end of the cannula body substantially to the distal end of the cannula body;
    (c) a rotatable mechanism located within the housing, comprising:
        a slide pusher assembly comprising a notch;
        a blade comprising an upper cutting surface that forms an upper angle with a bottom surface of the blade and a lower cutting surface that forms a lower angle with the bottom surface of the blade; and
        a substantially cylindrical body comprising a selector switch;
        wherein the blade resides at the notch of the slide pusher assembly in a pre-deployment position and wherein the selector switch allows engagement of the blade for deployment;
        wherein the blade comprises a tab that embeds into a pusher base; and
    (d) a tube assembly having a proximate end and a distal end, wherein the distal end of the tube assembly is located within the housing and extends through said cylindrical body, wherein the tube assembly connects to the slotted clear cannula from the proximate end of the cannula body,
        wherein the slotted clear cannula distal to the housing has a closed end that is tapered, and wherein the endoscopic surgical procedure is selected from the group consisting of carpal tunnel release, cubital tunnel release, plantar fascia release, lateral release for patella realignment, release of radial tunnel, release of pronatar teres, release of trigger finger, release of lacertous fibrosis, release of extensor tendons for lateral epicondylitis, release of medial epicondylitis, release of posterior and other compartments of a leg, forearm fascia release for fascial compartment syndrome, and release of fascial compartments in an upper and a lower extremity.

2. A device for an endoscopic surgical procedure, comprising:
(a) a housing having a proximate end and a distal end;
(b) a slotted tube attached to the distal end of the housing, the slotted tube comprising a tube body having a proximate end and a distal end, and a slot extending from the proximate end of the tube body substantially to the distal end of the tube body;
(c) a mechanism located within the housing reversibly pivotable between at least two positions, the mechanism comprising:
 a slide pusher assembly comprising a notch;
 a blade comprising an upper cutting surface that forms an upper angle with a bottom surface of the blade and a lower cutting surface that forms a lower angle with the bottom surface of the blade; and
 a substantially cylindrical body comprising a selector switch;
wherein the blade resides at the notch of the slide pusher assembly in a pre-deployment position and wherein the selector switch allows engagement of the blade for deployment;
wherein the blade comprises a tab that embeds into a pusher base; and
(d) a tube mounting assembly having a proximate end and a distal end, wherein the distal end of the tube mounting assembly is located within the housing and extends through said cylindrical body, wherein the tube mounting assembly is connected to the slotted tube from the proximate end of the tube body,
wherein the slotted tube is transparent,
wherein the slotted tube distal to the housing has a closed end that is tapered, and
wherein the endoscopic surgical procedure is selected from the group consisting of carpal tunnel release, cubital tunnel release, plantar fascia release, lateral release for patella realignment, release of radial tunnel, release of pronatar *teres*, release of trigger finger, release of lacertous fibrosis, release of extensor tendons for lateral epicondylitis, release of medial epicondylitis, release of posterior and other compartments of a leg, forearm fascia release for fascial compartment syndrome, and release of fascial compartments in an upper and a lower extremity.

\* \* \* \* \*